(12) United States Patent
Hiserodt et al.

(10) Patent No.: US 7,025,997 B2
(45) Date of Patent: Apr. 11, 2006

(54) COOLANT PLANT EXTRACT COMPOSITIONS CONTAINING MONOMENTHYL SUCCINATE

(75) Inventors: Richard Dwyer Hiserodt, Edison, NJ (US); Thumplasseril V. John, Morganville, NJ (US); Jide Adedeji, Bridgewater, NJ (US); Markus A. Eckert, Ramsey, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/671,411

(22) Filed: Sep. 24, 2003

(65) Prior Publication Data
US 2005/0064052 A1    Mar. 24, 2005

(51) Int. Cl.
    *A61K 35/78*    (2006.01)
(52) U.S. Cl. .................................... 424/747; 424/425
(58) Field of Classification Search .............. 424/747, 424/725
    See application file for complete search history.

(56) References Cited

U.S. PATENT DOCUMENTS

| | | | |
|---|---|---|---|
| 3,111,127 A | 11/1963 | Jarboe | |
| 3,644,613 A | 2/1972 | Demont et al. | |
| 3,793,446 A | 2/1974 | Moeller et al. | |
| 3,793,463 A | 2/1974 | Moeller et al. | |
| 3,830,930 A | 8/1974 | Moeller et al. | |
| 3,917,613 A | 11/1975 | Humbert et al. | |
| 3,991,178 A | 11/1976 | Humbert et al. | |
| 4,029,759 A | 6/1977 | Humbert et al. | |
| 4,032,661 A | 6/1977 | Rowsell et al. | |
| 4,033,994 A | 7/1977 | Watson et al. | |
| 4,044,120 A | 8/1977 | Rowsell et al. | |
| 4,059,118 A | 11/1977 | Watson et al. | |
| 4,069,345 A | 1/1978 | Gascoyne et al. | |
| 4,070,449 A | 1/1978 | Rowsell | |
| 4,070,496 A | 1/1978 | Rowsell et al. | |
| 4,136,163 A | 1/1979 | Watson et al. | |
| 4,136,164 A | 1/1979 | Rowsell et al. | |
| 4,150,052 A | 4/1979 | Watson et al. | |
| 4,157,384 A | 6/1979 | Watson et al. | |
| 4,178,459 A | 12/1979 | Watson et al. | |
| 4,190,643 A | 2/1980 | Watson et al. | |
| 4,193,936 A | 3/1980 | Watson et al. | |
| 4,226,988 A | 10/1980 | Watson et al. | |
| 4,296,093 A | 10/1981 | Rowsell et al. | |
| 4,880,630 A * | 11/1989 | Novak | |
| 5,009,893 A | 4/1991 | Cherukuri et al. | |
| 5,451,401 A | 9/1995 | Zerby et al. | |
| 5,451,404 A | 9/1995 | Furman | |
| 5,725,865 A | 3/1998 | Mane et al. | |
| 5,776,461 A * | 7/1998 | Pillai et al. | .................. 424/401 |
| 5,843,466 A | 12/1998 | Mane et al. | |
| 5,882,664 A * | 3/1999 | Soma et al. | |
| 6,121,315 A | 9/2000 | Nair et al. | |
| 6,627,233 B1 | 9/2003 | Wolf et al. | |
| 2003/0161802 A1 | 8/2003 | Flammer et al. | |
| 2004/0146483 A1 | 7/2004 | Golz-Berner et al. | |

FOREIGN PATENT DOCUMENTS

| | | |
|---|---|---|
| CA | 2064918 | 4/1992 |
| DE | 2608226 | 2/1978 |
| EP | 0 667 330 B1 | 8/1997 |
| JP | 7196439 | 1/1995 |
| WO | WO 87/03803 A1 * | 7/1987 |
| WO | WO 98/11867 | 3/1998 |

OTHER PUBLICATIONS

Derwent English abstract of CN 1174707 A—1998.*
http://davesgarden.com/pdb/go/63945—accessed Nov. 24, 2004.*
www.orient-hospital.com/Eng/gouji.htm—accessed Nov. 24, 2004.*
www.biosurvey.ou.edu/shrub/lyba4.htm—accessed Nov. 24, 2004.*
Watson, et al, New Compounds with the Menthol Cooling Effect, J.Soc. Cosmet.Chem. 29, 185-200, (1978).
Jablomer, et al, A Molecular Approach to Flavor Synthesis. I. Menthol Esters of Varying Size and Polarity, Journal of Polymer Science; Polymer Chemistry Edition, vol. 18, 2933-2940, (1980).
Kim S Y et al: "Taste and flavor compounds 1-4, 6-8 on box thorn (Lycium chinense Miller) leaves," 1997, Food Chemistry 1997 Correspondence (reprint) Address, M.Y. Jung, Dep. Of Food Sci. & Tech., Woosuk Univ., Samrea-Up, Wanju-Kun, Jeonbuk 565-800, Korea, vol. 58, NR. 4, p.(s)297-303.
Kolb N et al: "Analysis of sweet diterpene glycosides from Stevia Rebaudiana: Improved HPLC method" Journal of Agricultural and Food Chemistry, vol. 49, No. 10, Oct. 2001, pp. 4538-4541.
Kim et al., "Taste and flavor compounds in box thorn (*Lycium chinense* Miller) leaves", Food Chemistry 1997 58(4) :297-303.

* cited by examiner

*Primary Examiner*—Susan D. Coe
(74) *Attorney, Agent, or Firm*—Joseph F. Leightner

(57) ABSTRACT

The present invention relates to plant extracts containing a monomenthyl succinate for use as a coolant in food and non-food products. Methods for isolating the plant extracts are also provided.

6 Claims, 18 Drawing Sheets

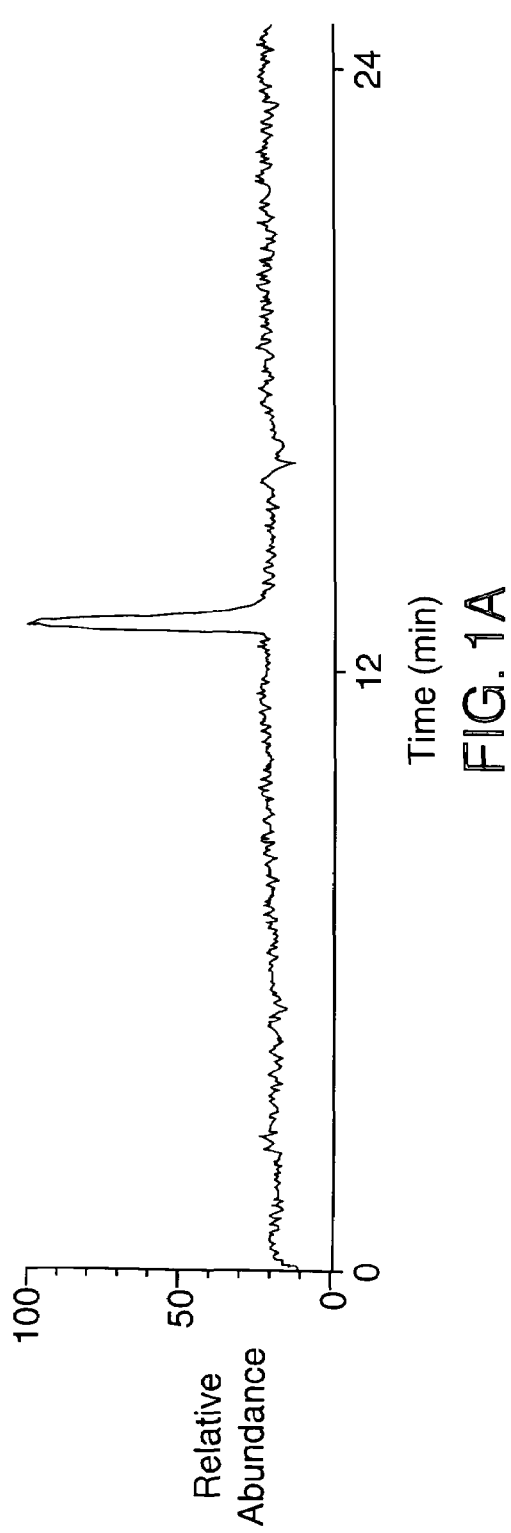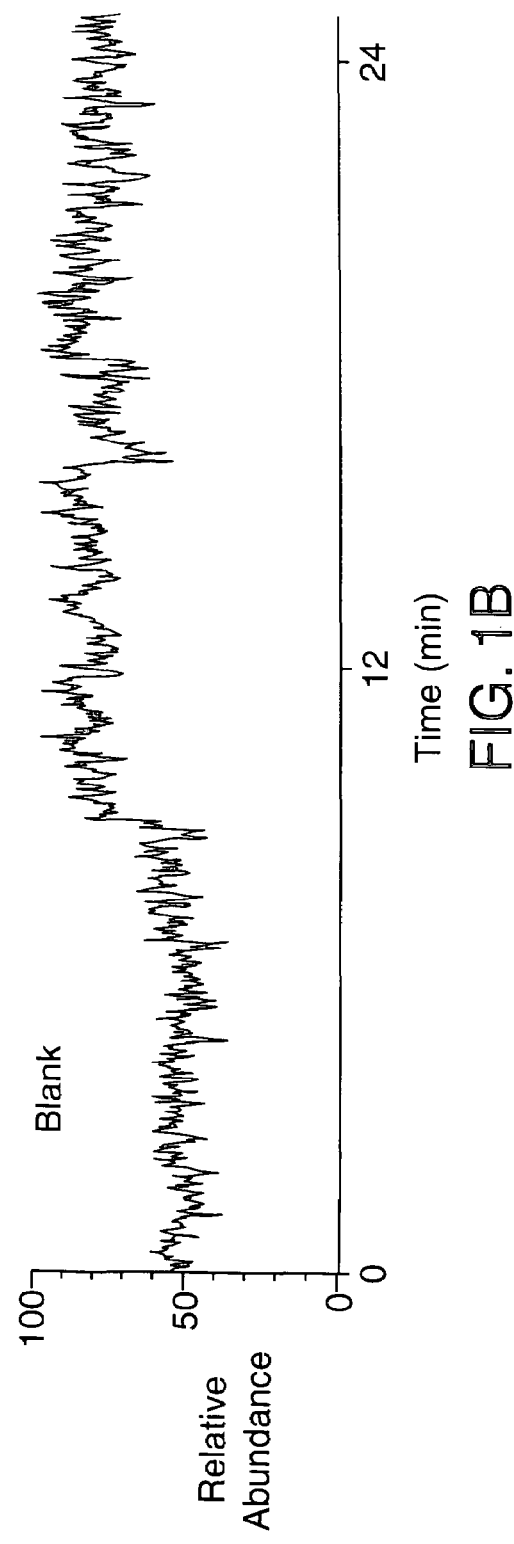

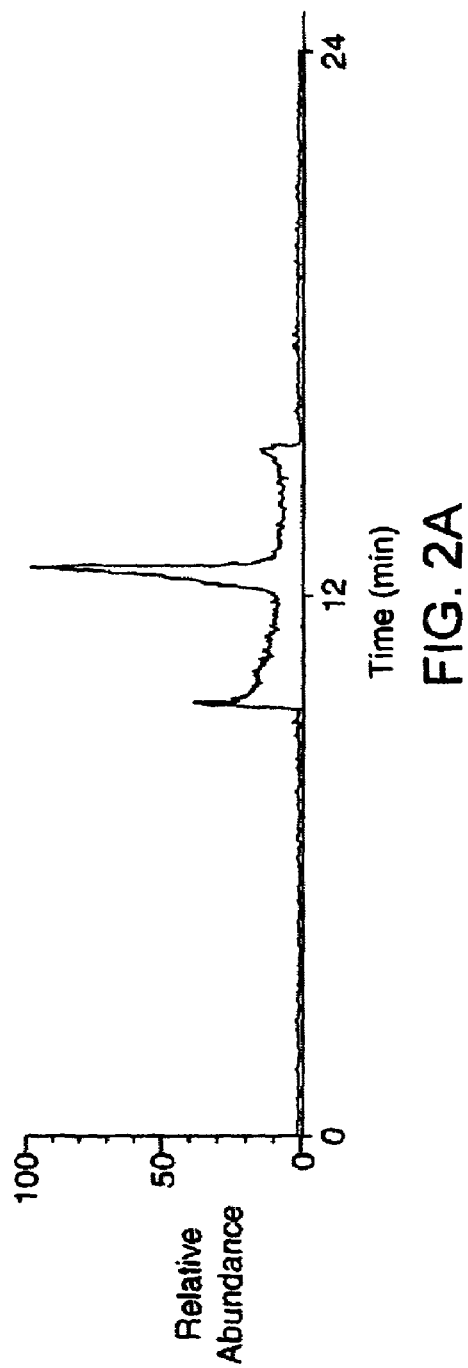
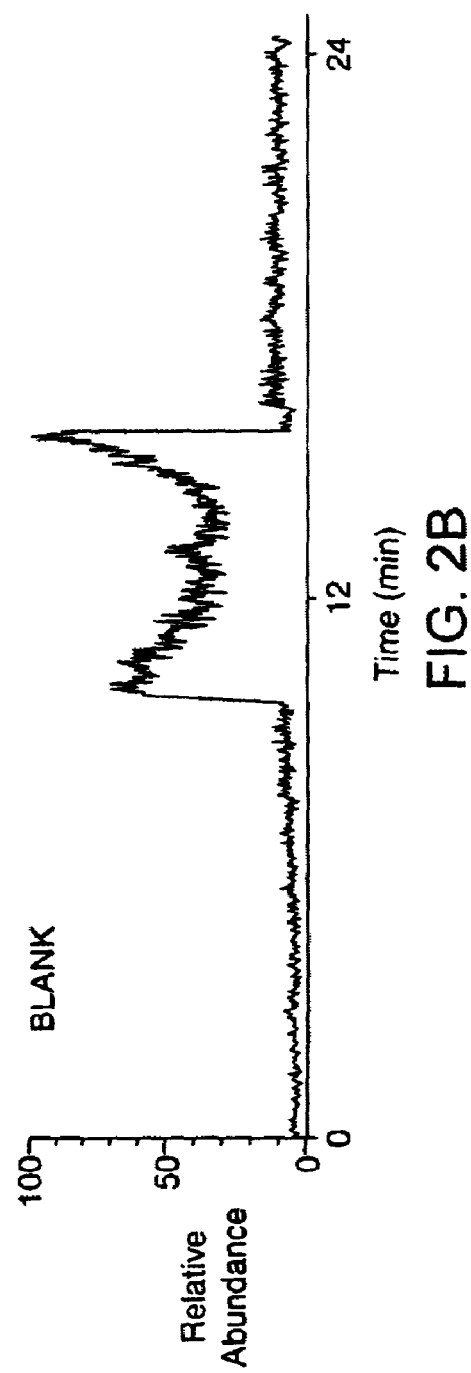
FIG. 2A
FIG. 2B

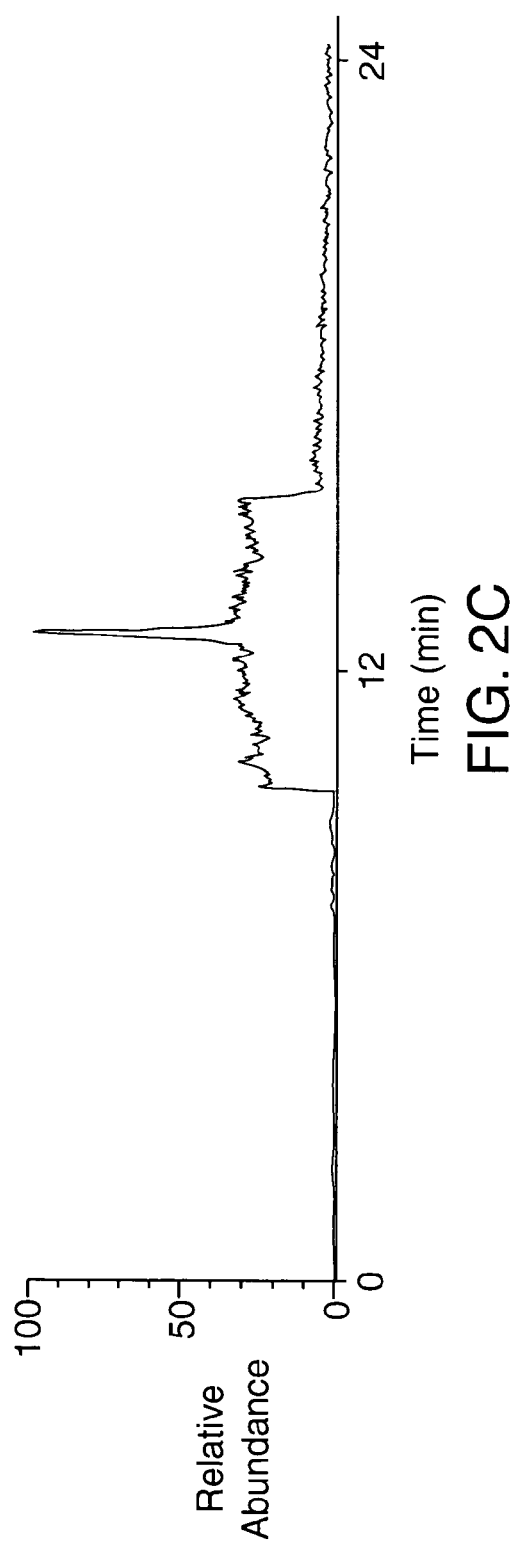
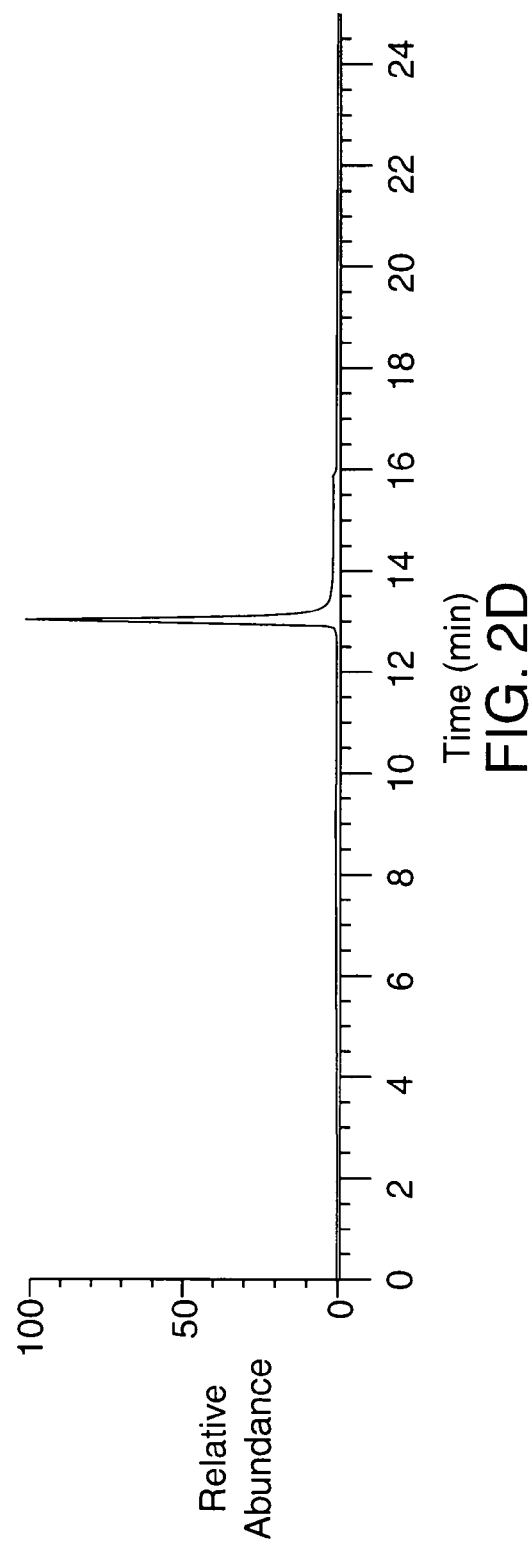

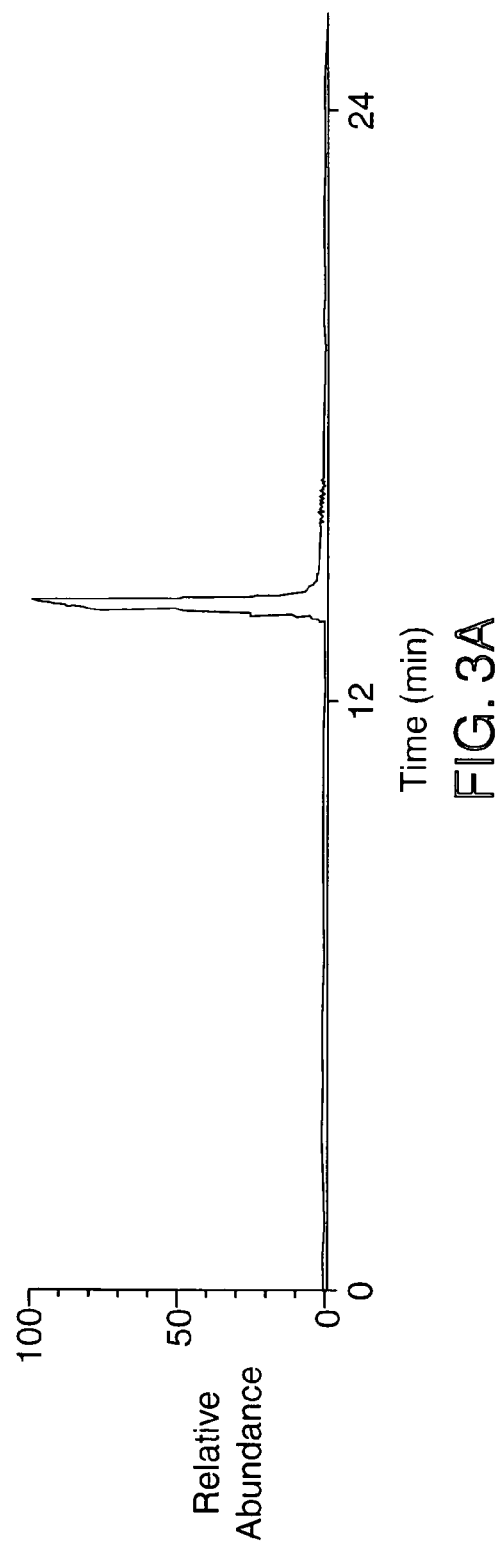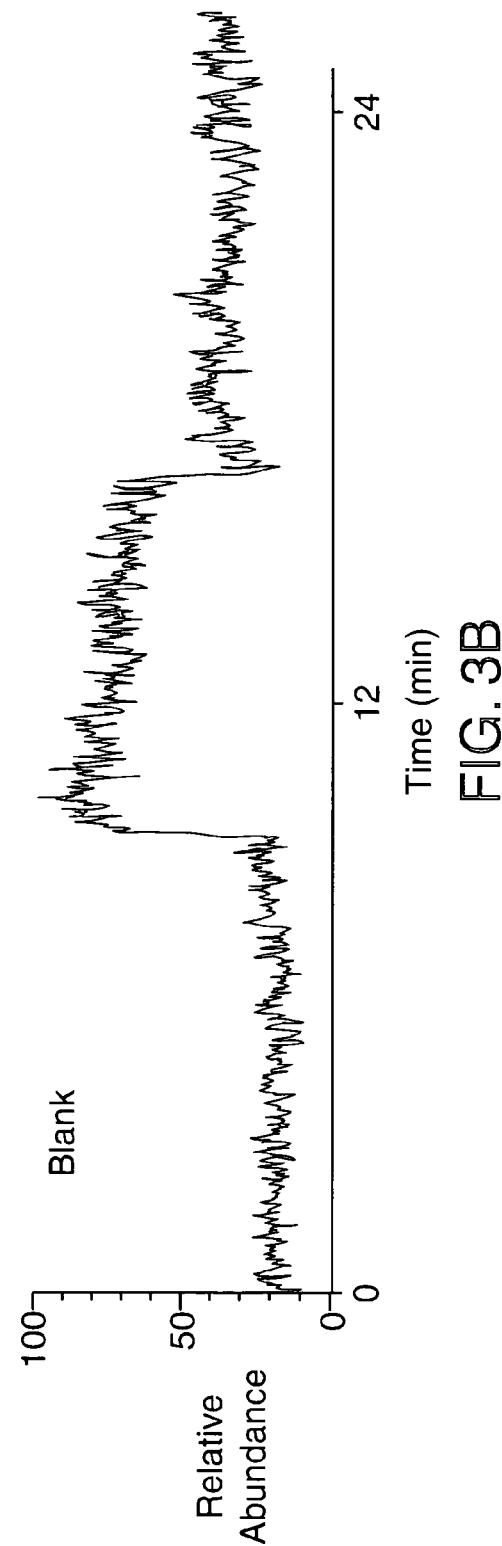

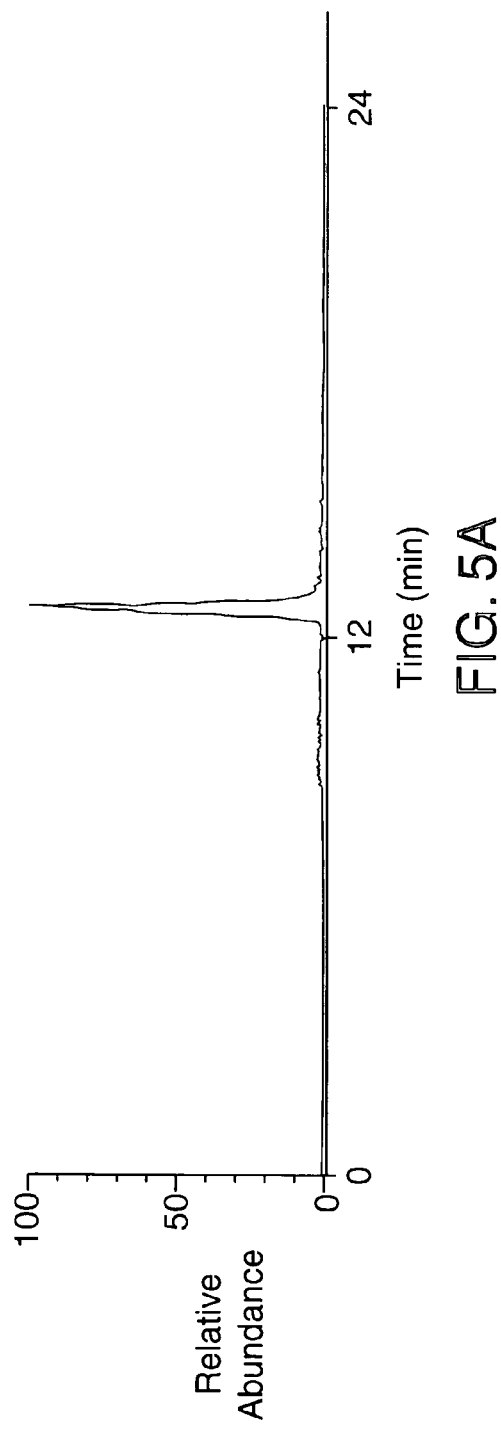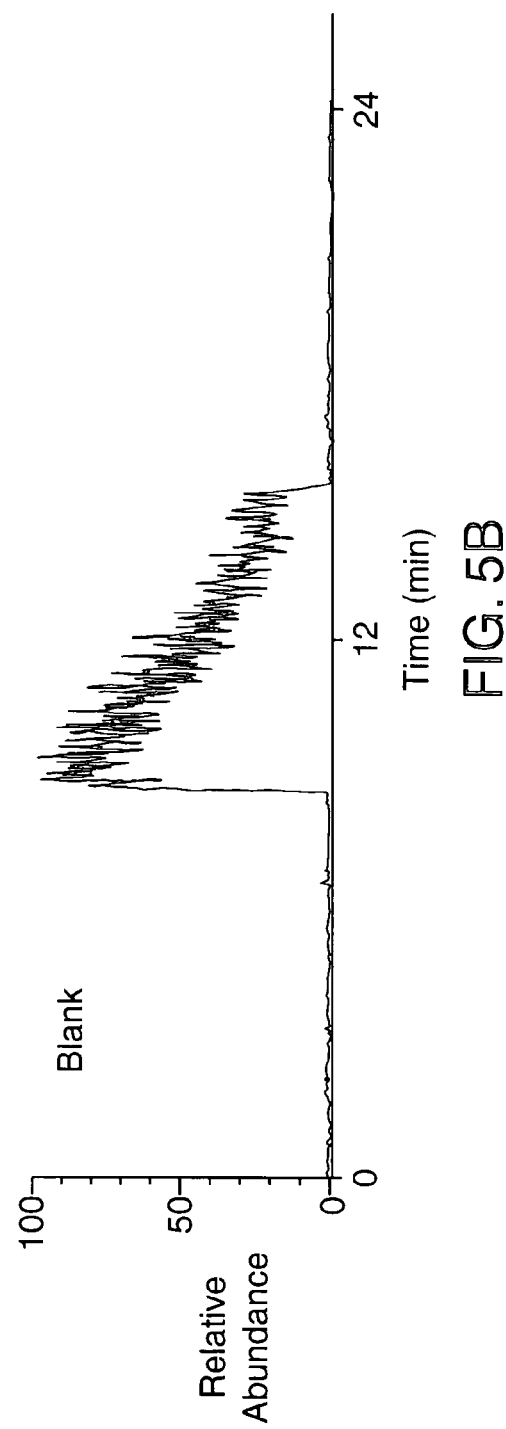

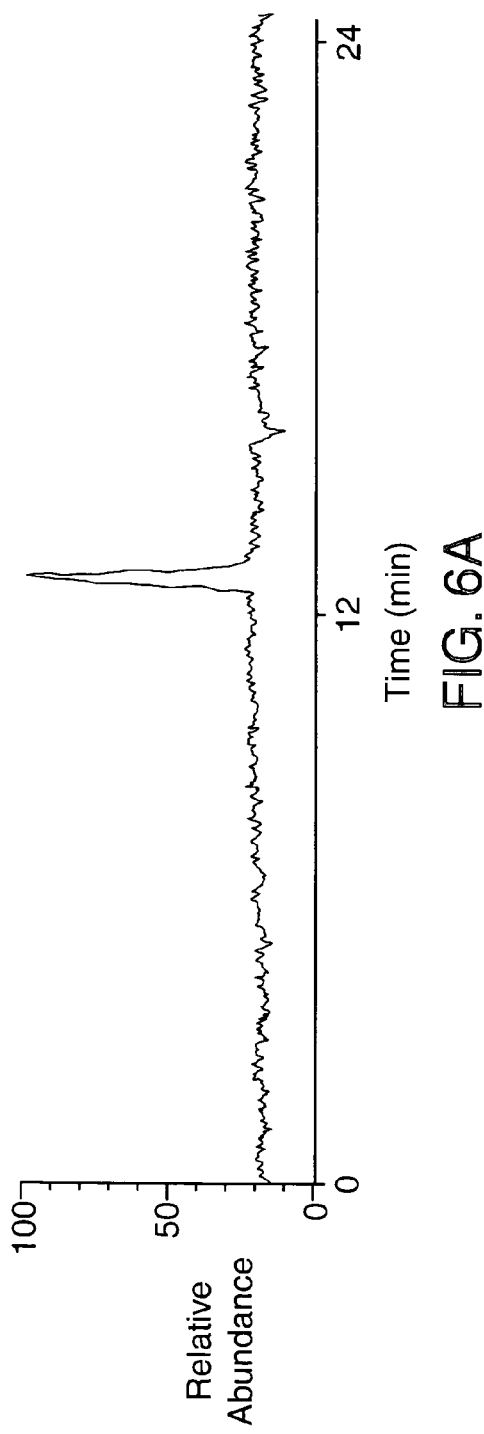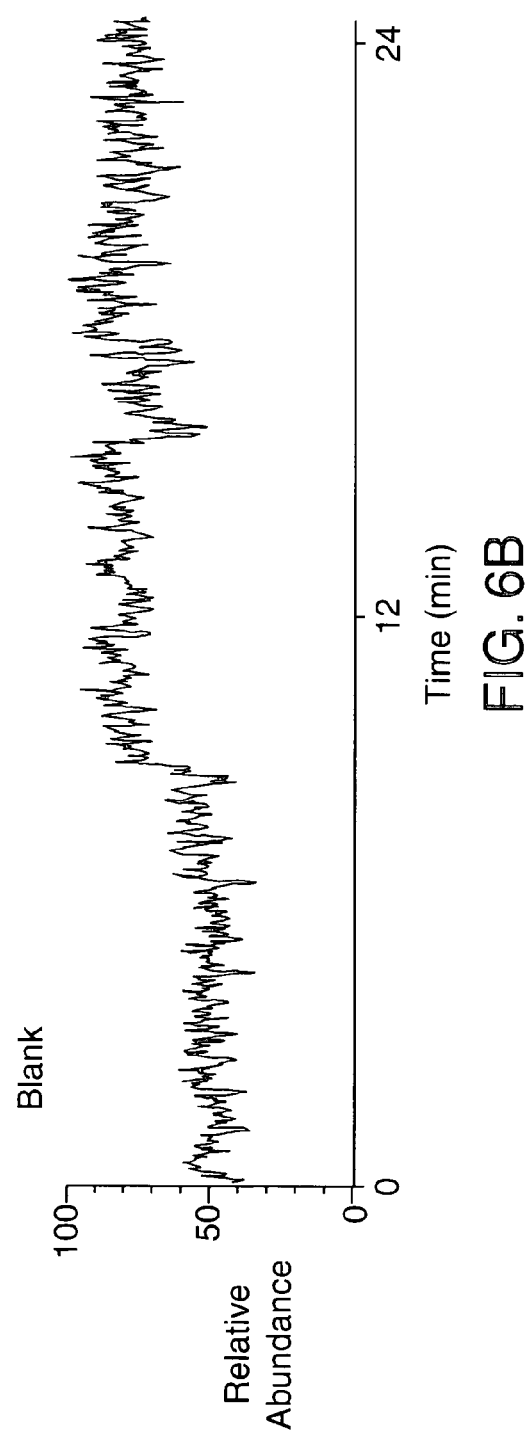

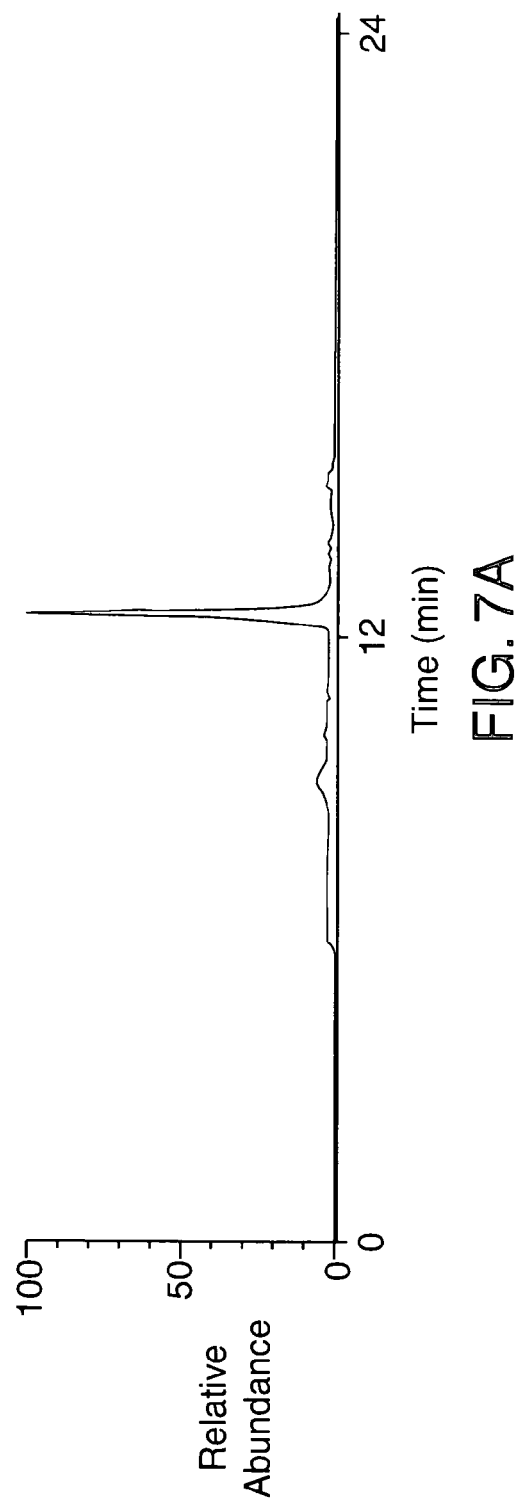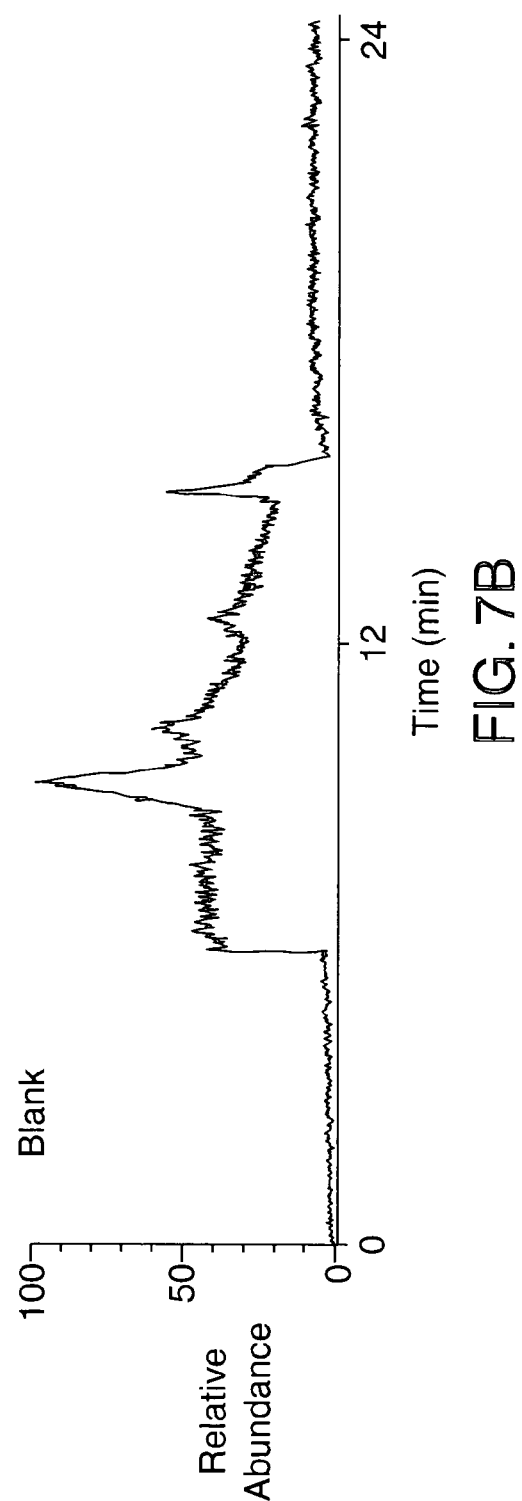

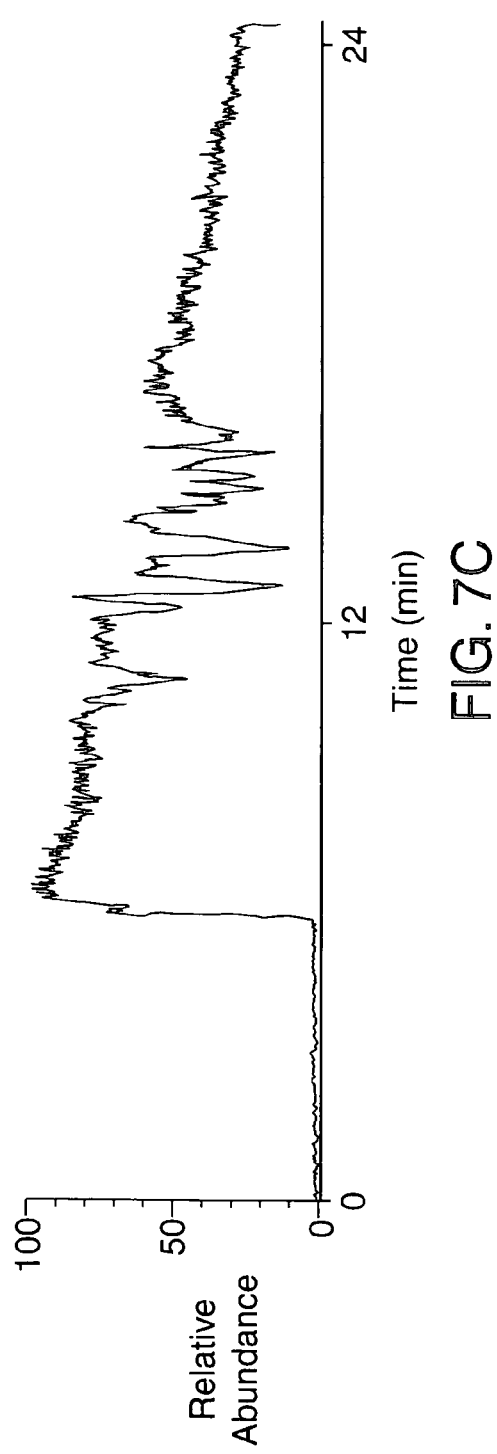
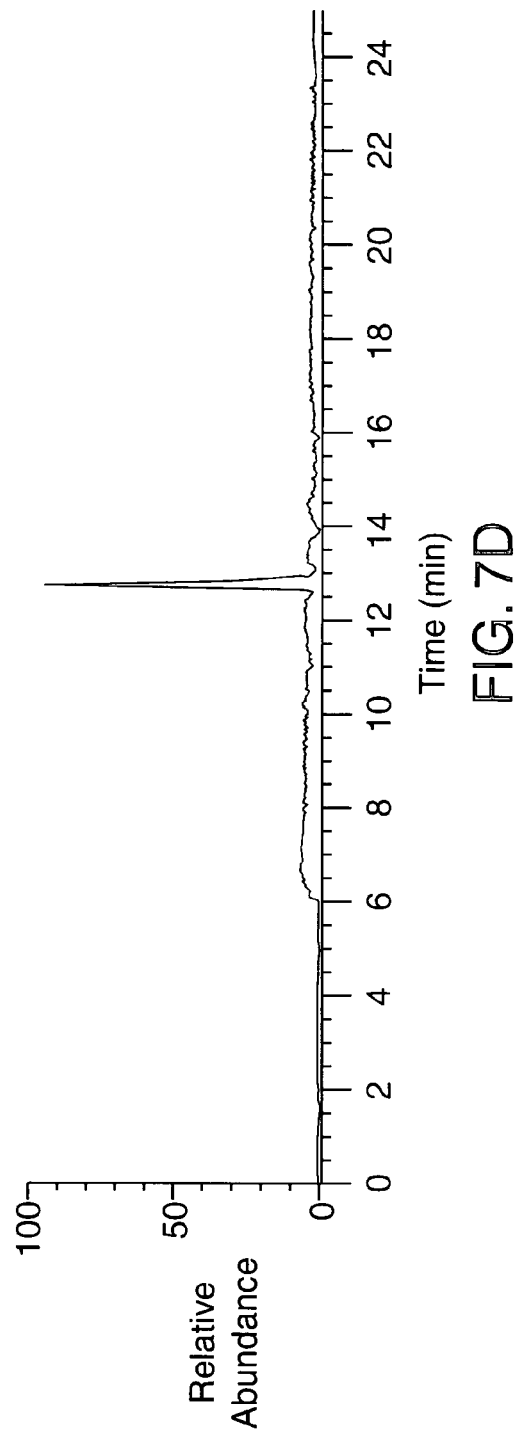

COOLANT PLANT EXTRACT COMPOSITIONS CONTAINING MONOMENTHYL SUCCINATE

BACKGROUND OF THE INVENTION

Monomenthyl succinate (MMS), also known as butanedioic acid monomenthyl ester, is a flavor compound utilized for its cooling effects in oral health care products and chewing gum, see U.S. Pat. Nos. 5,725,865 and 5,843,466. MMS is generally recognized as safe (GRAS) for products sold in the United States. Currently, MMS is synthetically produced for commercial use.

However, MMS can not be marketed as nature identical since its presence in natural sources has not been demonstrated. This limits the marketing of MMS-containing products in some countries. Therefore it would be desirable to find a natural source of MMS.

SUMMARY OF THE INVENTION

One aspect of the present invention is a plant extract composition containing monomenthyl succinate that is useful as a coolant. The plant extract is preferably isolated from a plant of the genus *Lycium* or *Mentha*, most preferably, *Lycium barbarum* or *Mentha piperita*.

Another aspect of the present invention is a method for isolating a plant extract containing monomenthyl succinate. The method involves mixing plant biomass, from a selected plant, with a solvent; extracting the mixture; and filtering the mixture to remove the plant biomass. In preferred embodiments, the solvent is ethanol and the selected plant is from the genus *Lycium* or *Methna*, more preferably, *Lycium barbarum* or *Mentha piperita*. The coolant plant extract of the present invention is useful in food ingredients and food products, as well as a variety of non-food products.

BRIEF DESCRIPTION OF THE DRAWINGS

FIG. 1A shows a LC/MS/MS chromatogram of 0.62 μg/mL MMS.

FIG. 1B shows a LC/MS/MS chromatogram of a blank (sample solvent).

FIG. 2A shows a LC/MS/MS chromatogram of 0.17 μg/mL MMS.

FIG. 2B shows a LC/MS/MS chromatogram of a blank (sample solvent).

FIG. 2C shows a LC/MS/MS chromatogram of 0.5 gram/mL *L. barbarum* fruit extract.

FIG. 2D shows a LC/MS/MS chromatogram of 250 μL *L. barbarum* fruit extract (0.5 gram/mL) spiked with 5 μL MMS (84 μg/mL).

FIG. 3A shows a LC/MS/MS chromatogram of 1.78 μg/mL MMS.

FIG. 3B shows a LC/MS/MS chromatogram of a blank (sample solvent).

FIG. 5A shows a LC/MS/MS chromatogram of 1.35 μg/mL MMS.

FIG. 5B shows a LC/MS/MS chromatogram of a blank (sample solvent).

FIG. 6A shows a LC/MS/MS chromatogram of 0.62 μg/mL MMS.

FIG. 6B shows a LC/MS/MS chromatogram of a blank (sample solvent).

FIG. 7A shows a LC/MS/MS chromatogram of 0.68 μg/mL MMS.

FIG. 7B shows a LC/MS/MS chromatogram of a blank (sample solvent).

FIG. 7C shows a LC/MS/MS chromatogram of flour extract injected as is.

FIG. 7D shows a LC/MS/MS chromatogram of 250 μL flour extract spiked with 1 μL MMS (68 μg/mL).

equation:

$$Y=0.35X+1.63; R^2=0.992; MMS_{ppm}=5.$$

Figure 10:
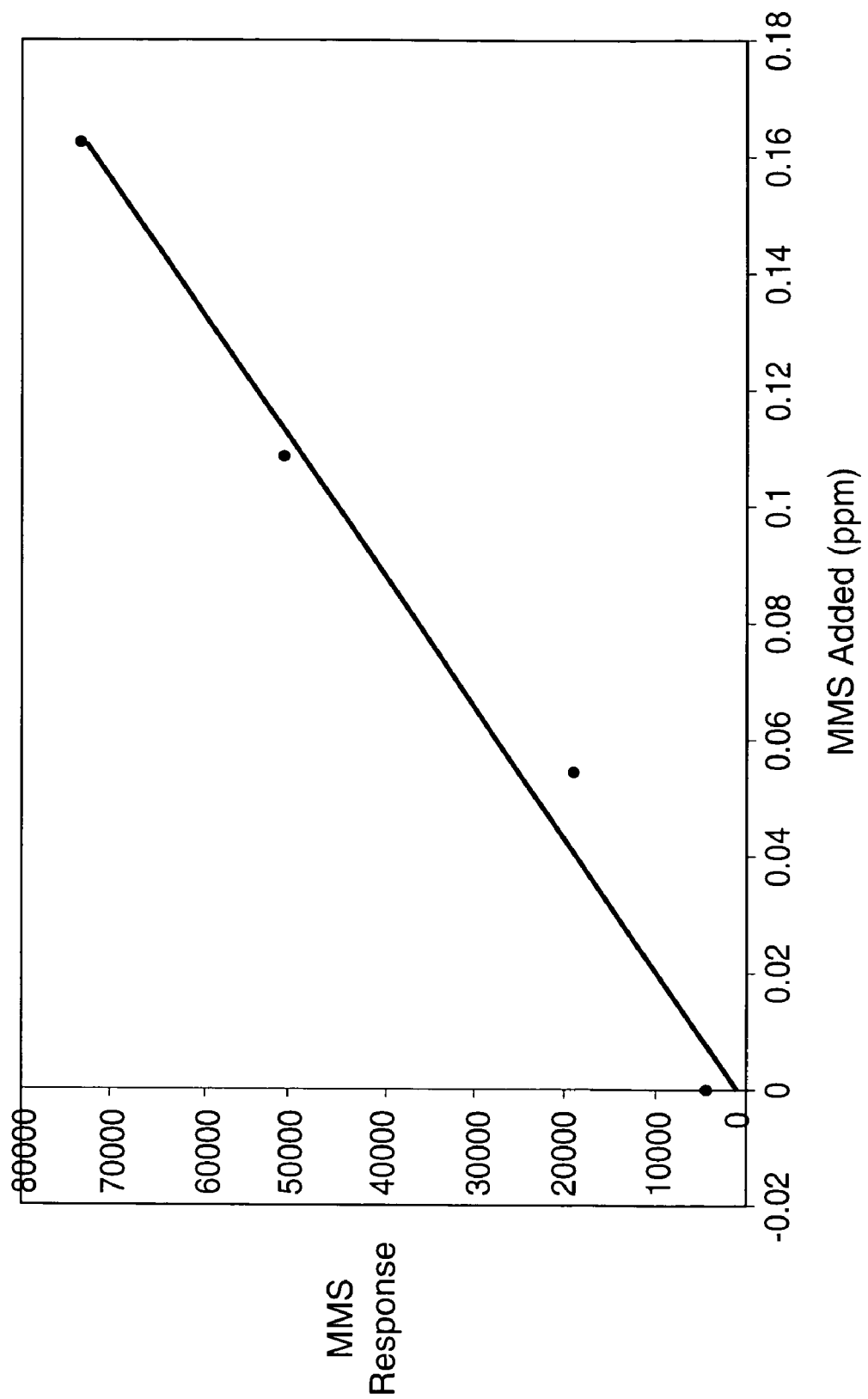

FIG. 10 shows a determination of MMS in flour extract by standard addition. Regression analysis:

equation:

$$Y=15.20X-0.097; R^2=0.922; MMS_{ppm}=0.006.$$

DETAILED DESCRIPTION OF THE INVENTION

It has now been shown that MMS is present in natural plant extracts such as *L. barbarum* fruit (FIGS. 1 and 2), *M. piperita* leaves (FIGS. 3 and 4), and a Wm. Leman spearmint/peppermint residue from team distillation of mint (FIG. 6) as determined by a two-dimensional separation technique using high performance liquid chromatography (HPLC) interfaced with tandem mass spectrometry (LC/MS/MS). A plant extract from each plant sample was separated on an HPLC column fitted with a guard column. A divert valve was used so that only components eluting from the column in the retention time window for MMS would enter the mass spectrometer. MMS was identified in natural plant extracts, in the negative ion mode, using atmospheric pressure chemical ionization (−APCI) and selected reaction monitoring (SRM). The precursor ion was set to m/z 255, for the deprotonated molecule, and the product ion was set to m/z 99 with a scan rate of 0.25 second. SRM is similar to acquiring a full scan mass spectrum but the full spectrum is not obtained. Rather, only selected ions in the mass spectrum are monitored. This results in a high degree of specificity and sensitivity required for the analysis of trace compounds in complex matrices. For example, to detect a compound other than monomenthyl succinate, using the instrument conditions provided herein, the compound must be acidic, have a molecular weight equal to 256, fragment to produce a production at mz 99, and have the same retention time as MMS. Specificity may be increased by monitoring more than one product ion, however, MMS produces only one such ion to any significant extent. LC/MS/MS is fundamentally a comparison of chromatographic and spectrometric data. MMS was identified based on its retention time correlation with an authentic sample (chromatographic method) and its spectrometric properties (mass spectrum). Further, the extracts were spiked at an appropriate level so that if another compound with a slightly different retention time were detected, it would appear as a shoulder on one of the peaks.

The blank was sample solvent, methanol or ethanol. It was analyzed after the retention time of MMS was established. The data showed that there was no contamination or carryover from the previous injection including instrument artifacts that may have produced a signal that could be misinterpreted as MMS.

Extracts of dried *L. barbarum* fruit were prepared with ethanol, ethyl acetate, and methylene chloride. MMS was primarily detected in the ethanol extract. Ethanol was subsequently used in the extraction of dried *L. barbarum* and *M. piperita* leaves.

Figure 9:
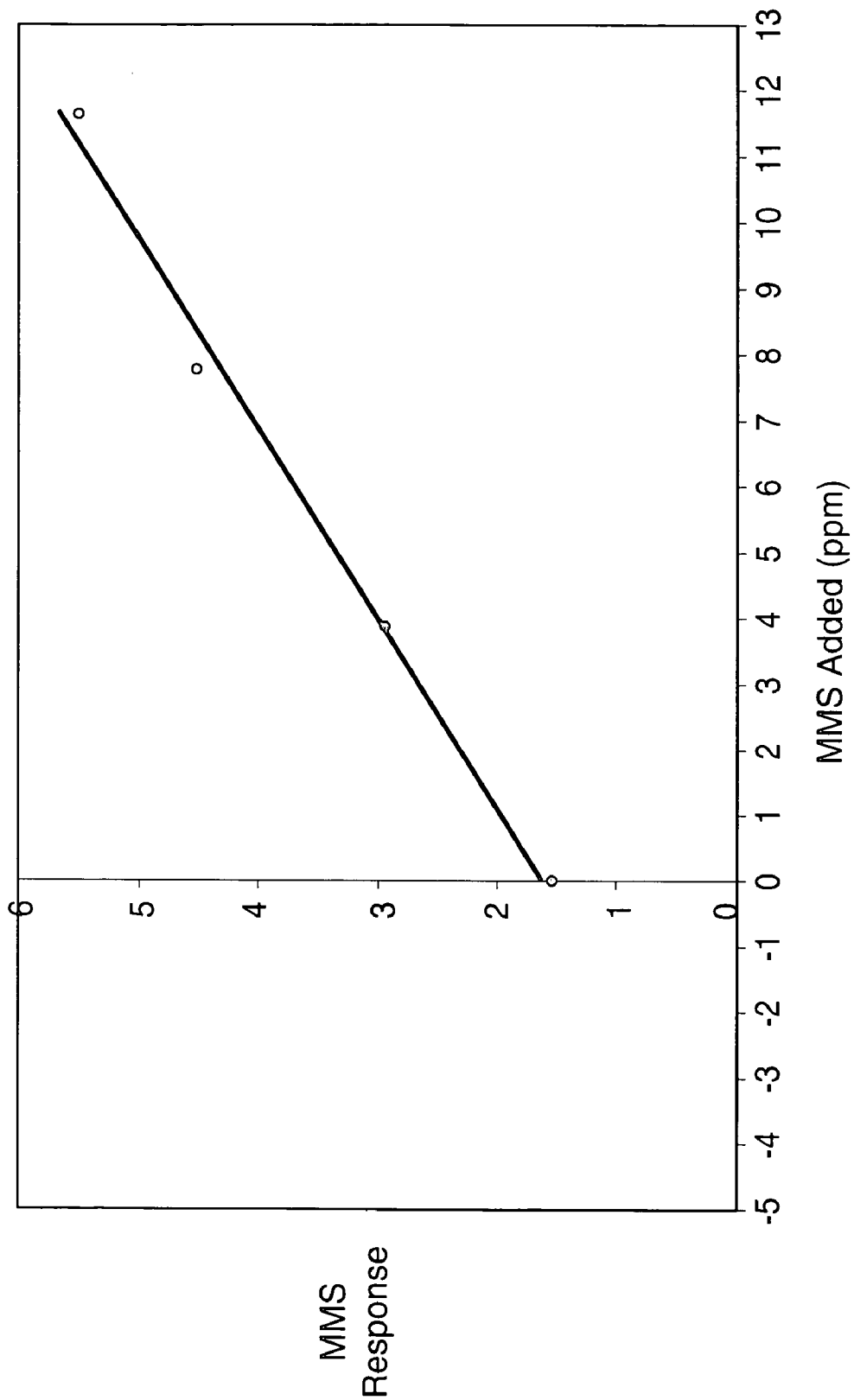
FIG. 9 shows a determination of MMS in *M. Piperita* extract by standard addition. Regression analysis.

To demonstrate that MMS was not an artifact of the extraction process, all-purpose flour was spiked with menthol and succinic acid and extracted following the procedure for extraction of *M. piperita* and *L. barbarum*. Two experiments were conducted; the first with a menthol spike at four times the level of MMS detected in *M. piperita* and a second at two times the level detected in *M. piperita*. The data showed that MMS was possibly detected at the noise level (FIGS. 7 and 8). Quantitative data obtained by standard addition showed the level of MMS in *M. piperita* extract to be 5 ppm (FIG. 9) while the MMS level in the flour extract was 0.006 ppm (FIG. 10). The level of MMS in *M. piperita* is more than 800 times the level in the extract of the spiked flour. While it may be possible that some of the MMS detected was the result of the extraction process, the majority of MMS detected was extracted from *M. piperita*. This is further supported by analysis of *L. barbarum* leaves (FIG. 5) which has been reported to contain menthol and succinic acid, however, MMS was not detected using the extraction process described herein. Menthol and succinic acid, precursors to MMS, have been shown to be present in *Lycium barbarum* leaves (Kim, et al. (1997) *Food Chemistry* 58:297–303). Further, *Mentha piperita* is also known to contain menthol.

The extraction of *L. barbarum* and *M. piperita* were performed in duplicate by different individuals. The analytical data showed the recovery of MMS from these natural plant extracts to be reproducible.

Accordingly, the present invention relates to a plant extract containing monomenthyl succinate (MMS) for use as coolant and methods for isolating the same. The composition of the invention is characterized as a plant extract which has cooling properties for a broad range of uses. As used herein, plant extract refers to a substance derived from a plant source, including modifications thereof, and which may be obtained using the general methods recited herein and other equivalent methods generally known in the art. In a preferred embodiment the plant extract contains a monomenthyl succinate or derivative thereof, such as monomenthyl sodium succinate, monomenthyl potassium succinate, monomenthyl lithium succinate, monomenthyl calcium succinate, monomenthyl magnesium succinate or monomenthyl barium succinate. Such derivatives may be isolated from a plant source or generated by chemically modifying a parent compound that has been isolated from a plant source.

The plant extract may be isolated from a selected plant of the family *Solanaceae* or *Lamiaceae*. More preferably, the plant extract is isolated from a selected plant of the genus *Lycium* (e.g., *L. afrum*, *L. shawii*, *L. barbarum*, *L. carolinianum*, *L. cestroides*, *L. chilense*, *L. chinense*, *L. depressum*, *L. europaeum*, *L. ferocissimum*, *L. flexicaule*, *L. foetidum*, *L. horridum*, *L. japonicum*, *L. oxycarpum*, *L. pallidum*, or *L. ruthenicum*) or *Mentha* (e.g., *M. villosa*, *M. aquatica*, *M. spicata*, *M. arvensis*, *M. canadensis*, *M. australis*, *M. cablin*, *M. longifolia*, *M. gracilis*, *M. cervina*, *M. piperita*, *M. cunninghamii*, *M. dahurica*, *M. dalmatica*, *M. diemenica*, *M. dumetorum*, *M. gattefossei*, *M. grandiflora*, *M. haplocalyx*, *M. suaveolens*, *M. japonica*, *M. kopetdaghensis*, *M. laxiflora*, *M. maximilianea*, *M. micrantha*, *M. muelleriana*, *M. villosa*, *M. rotundifolia*, *M. pulegium*, *M. requienii*, *M. rotundifolia*, *M. satureioides*, *M. smithiana*, *M. suaveolens*, or *M. verticillata*). This list of plants is by way of illustration only and is not intended, in anyway, to be a limitation thereof. Other plant sources useful to the present invention include any food and generally recognized as safe, commonly referred to as GRAS material, which contains appreciable amounts of a monomenthyl succinate. In a preferred embodiment, the plant extract is isolated from *L. barbarum* or *M. piperita*.

The plant extract composition of the invention, in general, isolated as follows: dried, powdered, or ground plant biomass is placed in an extraction vessel and mixed with a solvent. A solvent which may be used in accordance with a method of isolating a plant extract of the invention includes, but is not limited to, ethanol, acetone, ethyl acetate, methylene chloride or acetonitrile and may vary with the plant species selected. Most preferably, the solvent is ethanol. The mixture is extracted for a selected amount of time such as 10–24 hours, preferably 14 hours, and subsequently filtered to remove plant biomass. The plant extract may be used as a dilute extract or be concentrated by rotary evaporation, freeze-drying and the like for storage and later use. The plant extract may then be analyzed as described herein to evaluate the purity and content of coolant, i.e., monomenthyl succinate. It should be understood that modifications to the above-mentioned process may be made to increase the rate of processing or enhance the content of monomenthyl succinate in the plant extract.

In general, a coolant plant extract composition of the invention preferably contains between about 0.00005 percent (0.5 part per million, ppm) and about 0.1 percent (1000 ppm) monomenthyl succinate or the equivalent, wherein the percentages are on a weight basis. More preferably, a coolant plant extract composition contains between about 0.0001 percent (1 ppm) and about 0.001 percent (10 ppm) monomenthyl succinate and, most preferably, about 0.0005 percent (5 ppm) monomenthyl succinate. A plant extract composition of the present invention may be used in any composition where a coolant may be beneficial, including food ingredients and food products. See, for example, U.S. Pat. Nos. 5,725,865 and 5,843,466, herein incorporated by reference and WO 98/11867. Food ingredients broadly includes flavor systems, flavor enhancers, and other edible ingredients added to foods and food products. Foods and food products broadly include solid foods, liquid beverages, medicaments and other edible materials regardless of their specific form, including, but not limited to, alcoholic beverages, antacids, laxatives, or chewing gum. Further, the plant extract of the present invention is broadly applicable to a variety of non-food products including, for example, cosmetics, toiletries, oral care products, nasal care products, lotions, oils, ointments and perfumes. The plant extracts may be used as part of an ingredient system, an additive for foods or other products, and may be prepared in a dry (e.g., powdered) form or as a water, oil, or alcohol-based concentrate or syrup depending on the end use and the proposed method of addition. Further, the plant extract may be incorporated as a solid or an aqueous solution or syrup at various stages during the manufacture of food products, ingredients or other products. The amount of coolant plant extract incorporated into the end use composition will vary depending upon the content of monomenthyl succinate present in the plant extract, the particular derivative of monomenthyl succinate, the degree of cooling effect desired and the strength of other flavorants or additives in the composition.

The invention is described in greater detail by the following non-limiting examples.

EXAMPLE 1

Preparation of Extracts

Dried *L. barbarum* fruit was purchased from an Asian food store. Dried *M. piperita* and *L. barbarum* leaves were obtained from Plant It Herbs (Athens, Ohio, www.plantitherbs.com).

Figure 1C:
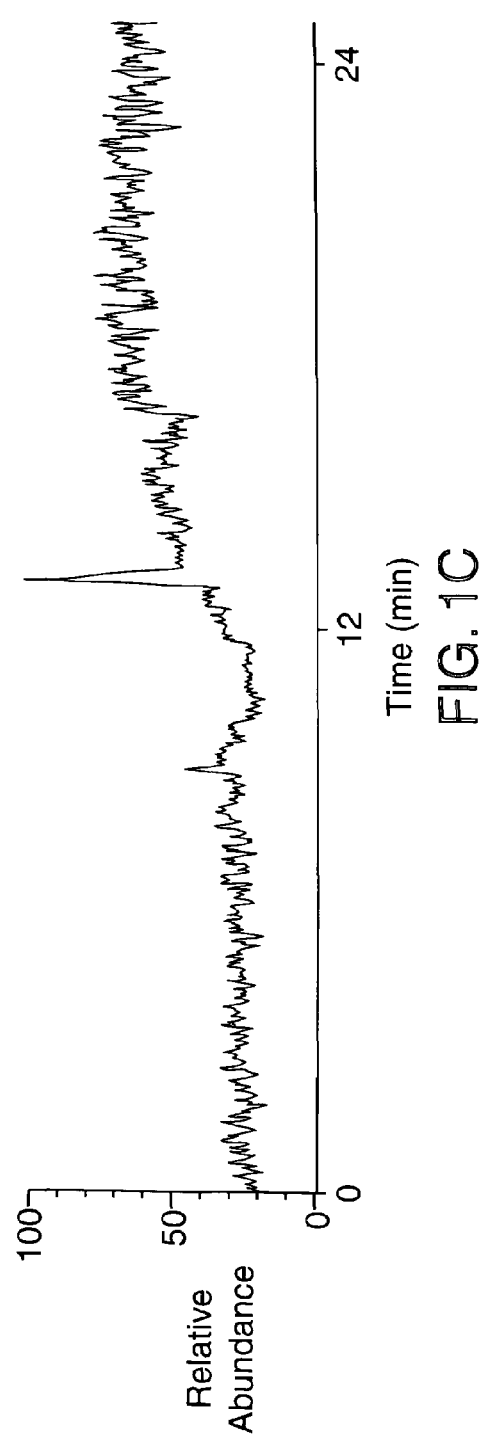
FIG. 1C shows a LC/MS/MS chromatogram of 0.6 gram/mL *L. barbarum* fruit extract.
Figure 1D:
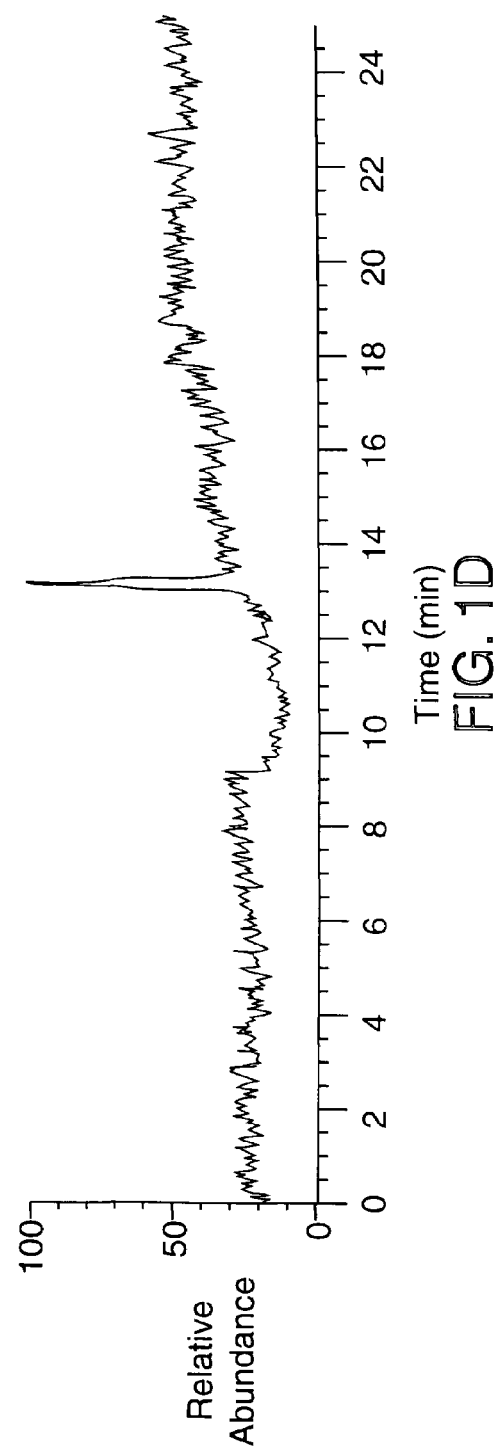
FIG. 1D shows a LC/MS/MS chromatogram of 250 μL *L. barbarum* fruit extract (0.6 gram/mL) spiked with 5 μL MMS (62 μg/mL).

Dried *L. barbarum* fruit was frozen overnight at −25° C. and powdered in a blender. The moisture content of the powder was determined using a Halogen Moisture Analyzer (Mettler HR 73 HMA) and found to be 16.58%. 205 Grams of powder was extracted in a glass soxhlet extractor using 800 mL of 95% ethyl alcohol. The soxhlet extraction continued for 13.5 hours over a period of two days (9 hours on day one and 4.5 hours on day two). The extract was filtered (Whatman filter paper 1) and the filtrate concentrated to 50 grams in a rotary evaporator (Buchi Rotavapor R-124) under vacuum at 55° C. and 100 rpm. The concentrate, on keeping overnight, developed a sediment which was filtered out to yield 25.5 grams of the final product. 1.3 Grams of this extract were diluted with 1.0 mL methanol for analysis (sample concentration=0.6 gram/mL assuming $d_{extract}$=1 gram/mL). FIG. 1 shows the results of this analysis.

In an identical extraction procedure, 200 grams of freshly powdered dried *L. barbarum* fruit yielded 84 grams of plant extract. However, in this procedure the fruit was not frozen prior to extraction. 1.7 Grams of extract were diluted with 2.0 mL ethanol for analysis (sample concentration=0.5 gram/mL assuming $d_{extract}$=1 gram/mL) FIG. 2 shows the results of this analysis.

Figure 3C:
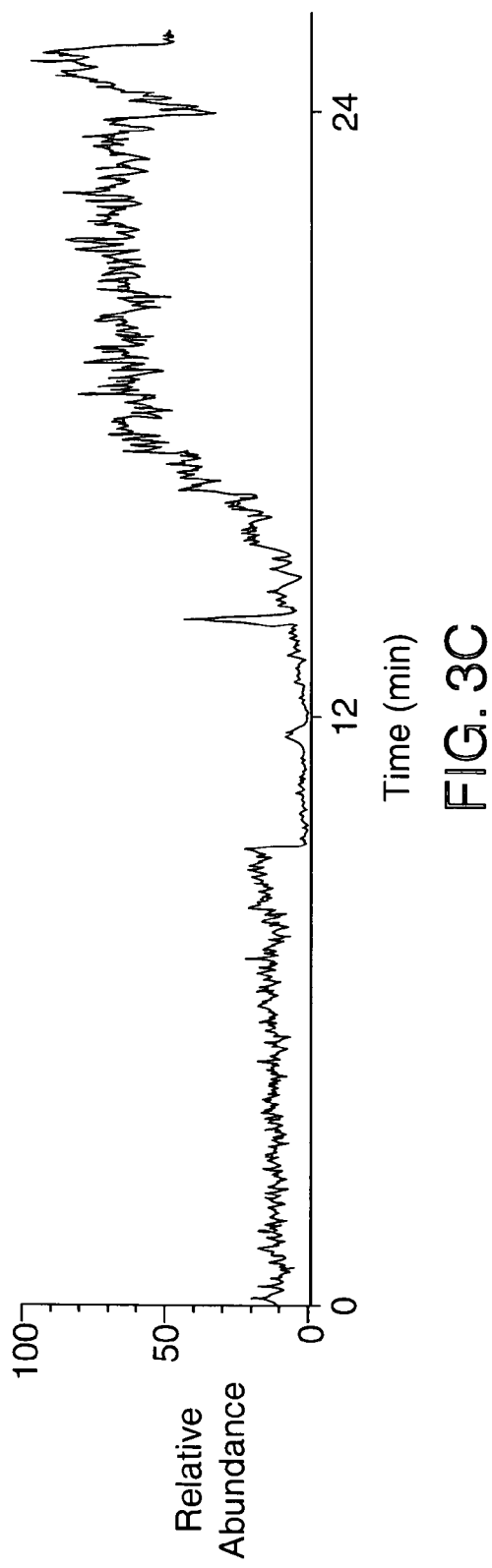
FIG. 3C shows a LC/MS/MS chromatogram of 0.6 gram/mL *M. piperita* leaf extract.
Figure 3D:
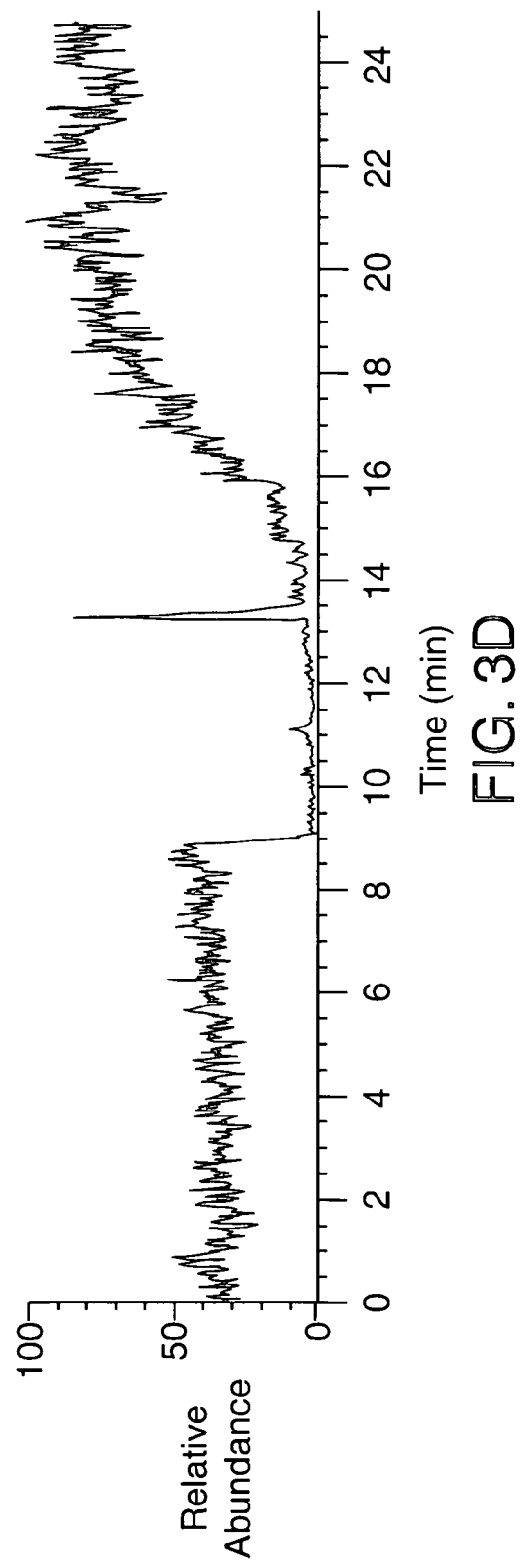
FIG. 3D shows a LC/MS/MS chromatogram of 250 μL *M. piperita* leaf extract (0.6 gram/mL) spiked with 2 μL MMS (178 μg/mL).
Figure 4A:
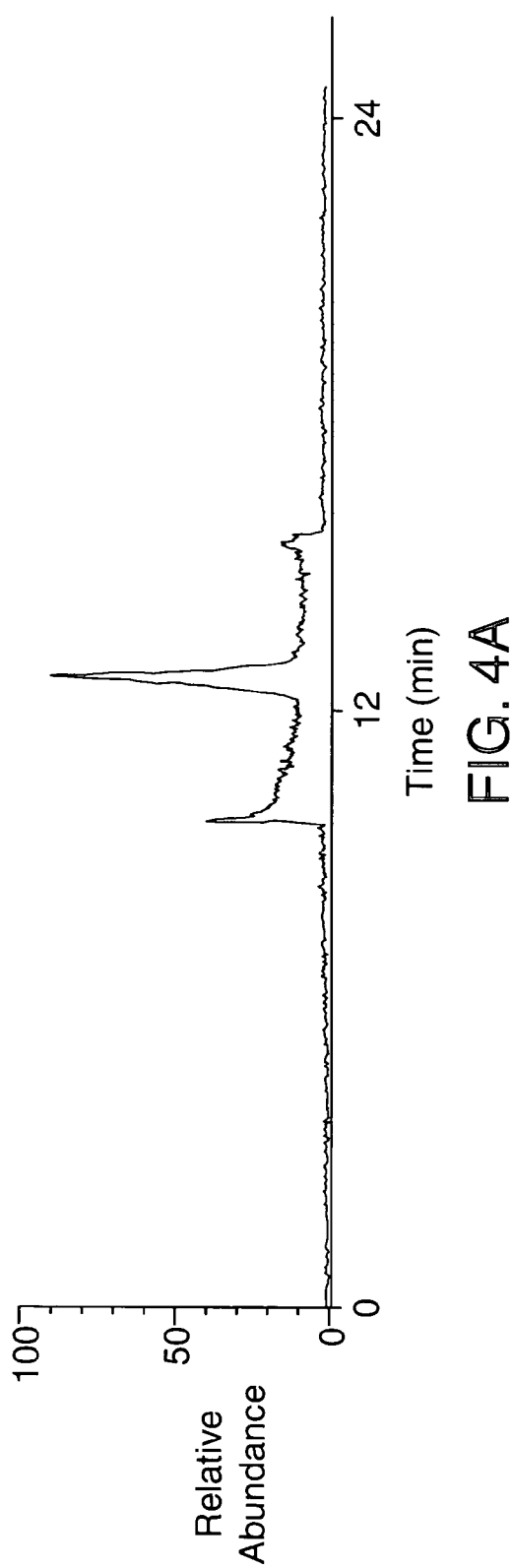
FIG. 4A shows a LC/MS/MS chromatogram of 0.17 μg/mL MMS.
Figure 4B:
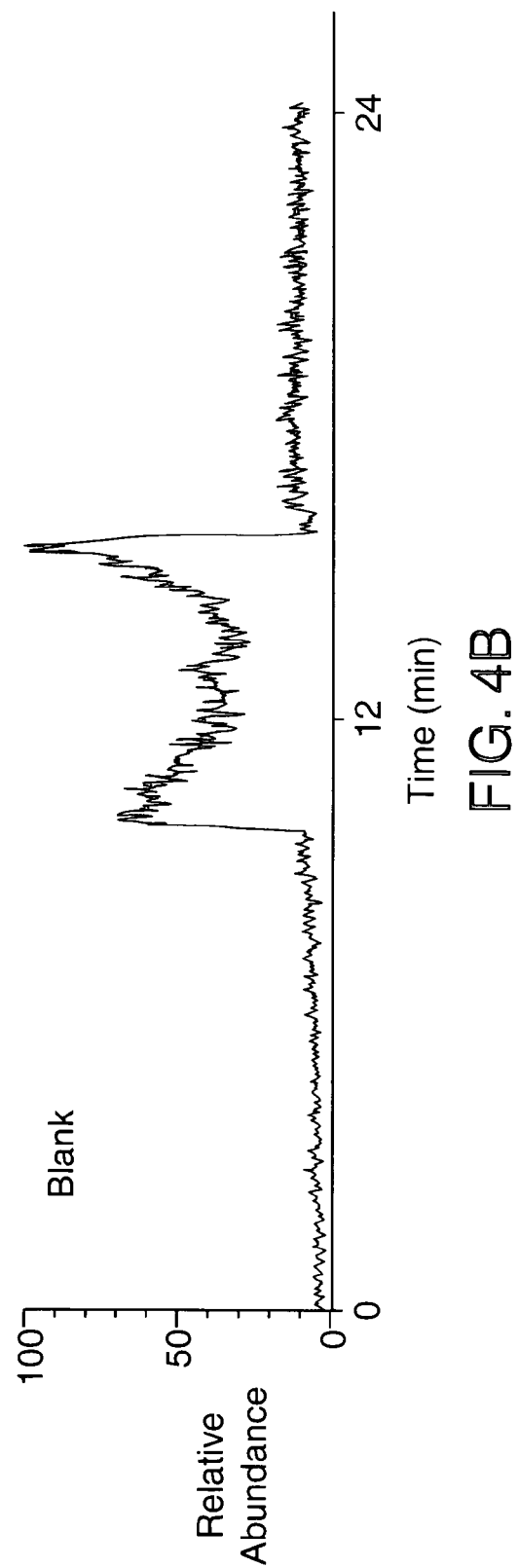
FIG. 4B shows a LC/MS/MS chromatogram of a blank (sample solvent).
Figure 4C:
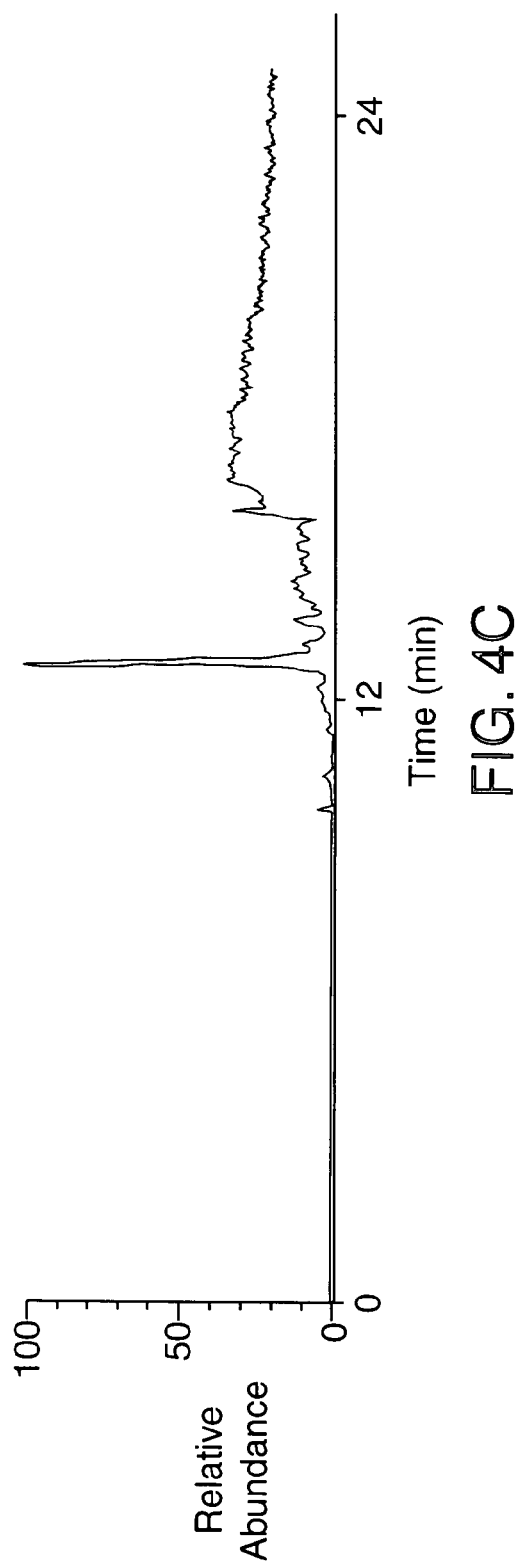
FIG. 4C shows a LC/MS/MS chromatogram of 0.5 gram/mL *M. piperita* leaf extract.
Figure 4D:
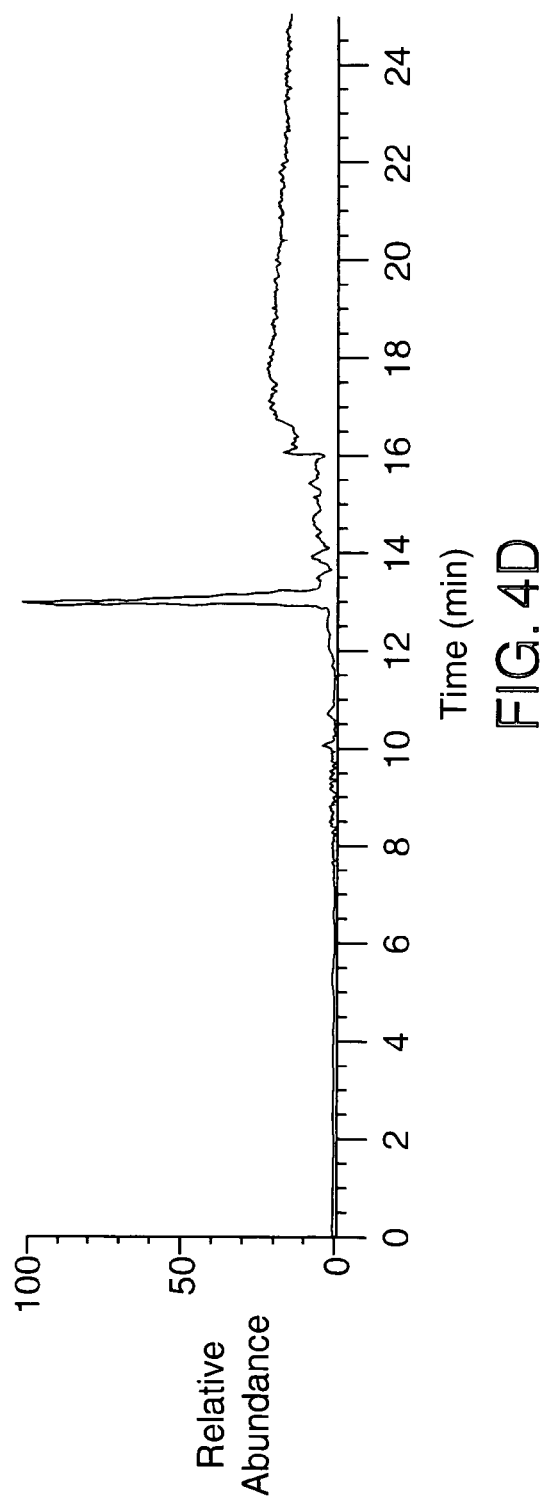
FIG. 4D shows a LC/MS/MS chromatogram of 250 μL *M. piperita* leaf extract (0.5 gram/mL) spiked with 5 μL MMS (84 μg/mL).

Dried *M. piperita* leaves were extracted using the same procedure as described for *L. barbarum* fruit and leaves, a further discussion of the leaves is provided hereinafter. However, because of the difference in the bulk density compared to the *L. barbarum* fruit and equipment size limitations, a smaller sample was extracted. 30.5 Grams of the powdered leaves were extracted to yield 6.1 grams of extract. The extract was directly analyzed but the signal to noise ratio was weak and the extraction was repeated with a larger sample. For the second extraction, 115 grams of the powdered leaves were extracted to yield 15 grams of plant extract. 1.4 Grams of this extract were diluted with 1.0 mL methanol for analysis (sample concentration=0.6 gram/mL assuming $d_{extract}$=1 gram/mL). FIG. 3 shows the results of this analysis.

Extraction of *M. piperita* leaves was repeated using 100 grams of dried leaves to yield 18 grams of plant extract. 1.8 Grams of sample were diluted with 2.0 mL ethanol for analysis (sample concentration=0.5 gram/mL assuming $d_{extract}$=1 gram/mL). FIG. 4 shows the results of this analysis.

Figure 5C:
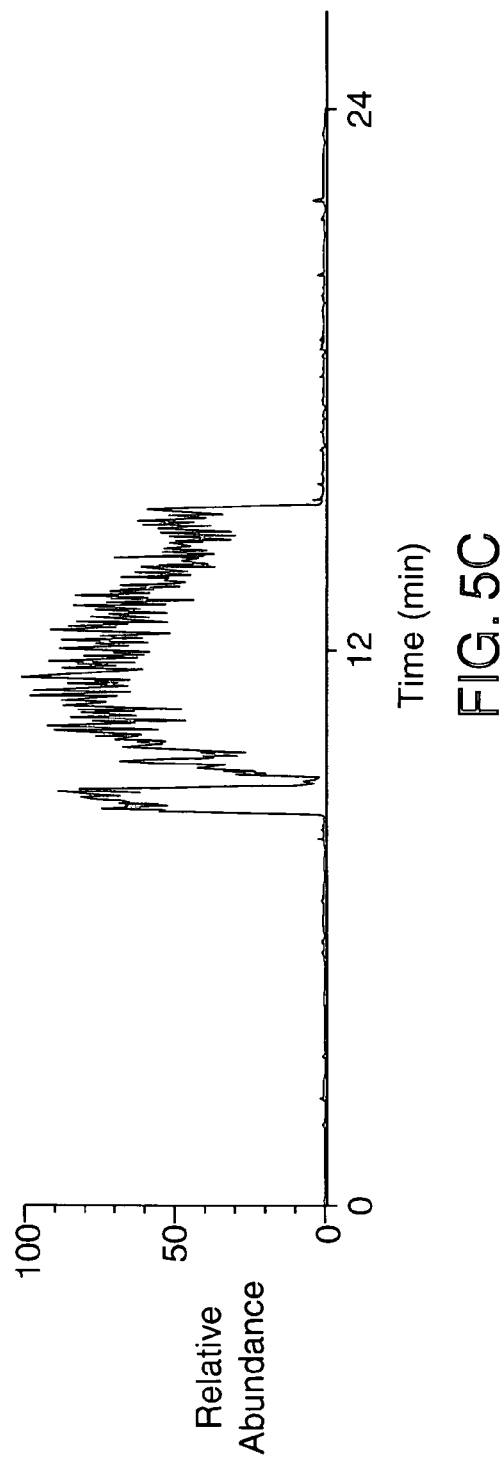
FIG. 5C shows a LC/MS/MS chromatogram of *L. barbarum* leaf extract injected without dilution prior, as is, to analysis.
Figure 5D:
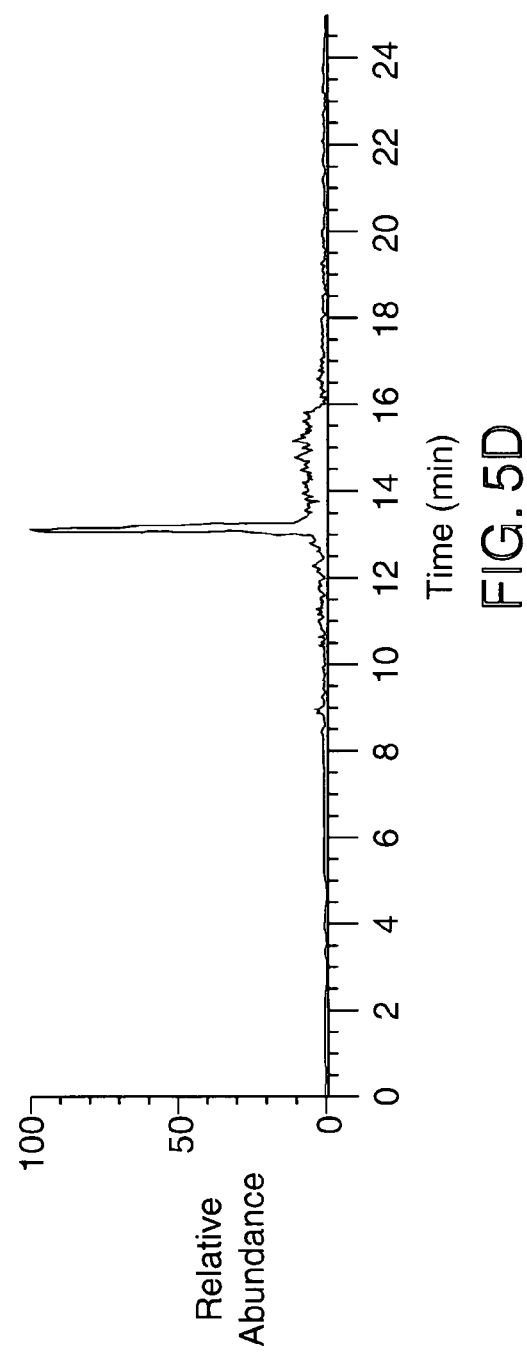
FIG. 5D shows a LC/MS/MS chromatogram of 250 μL *L. barbarum* leaf extract directly extracted without dilution prior to analysis which was spiked with 1 μL MMS (135 μg/mL).

Dried *L. barbarum* leaves were extracted using the procedure described for *L. barbarum* fruit. 50.5 Grams of dried leaves were extracted to yield 6.6 grams of extract. The extract was directly analyzed, without dilution, for the presence of MMS. FIG. 5 shows the results of this analysis.

Figure 6C:
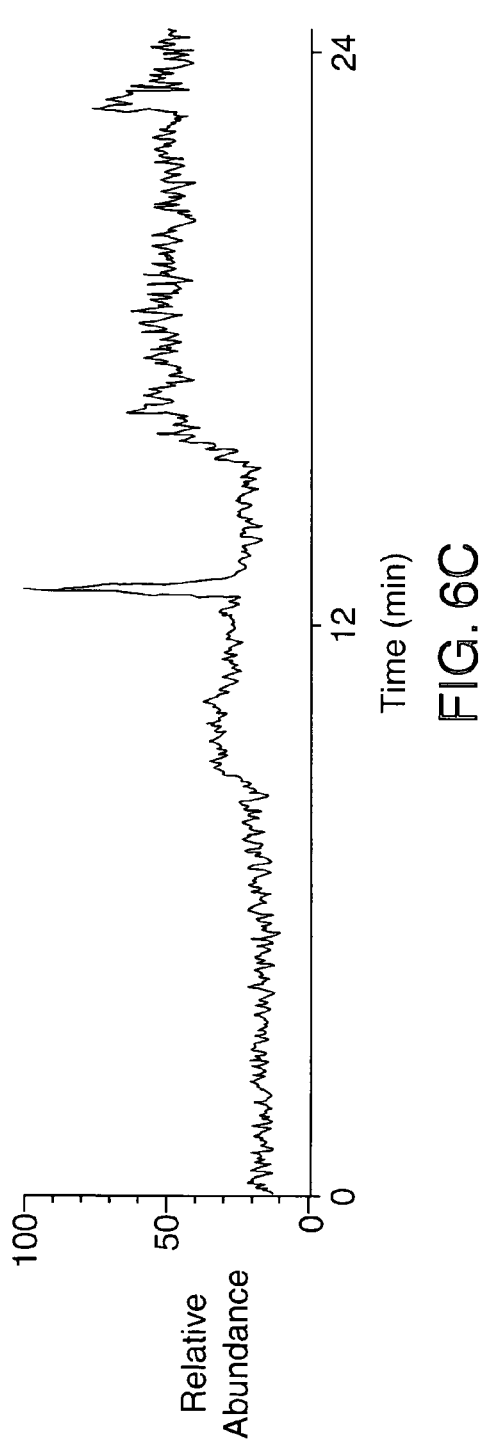
FIG. 6C shows a LC/MS/MS chromatogram of 0.2 gram/mL Wm. Leman spearmint/peppermint residue.
Figure 6D:
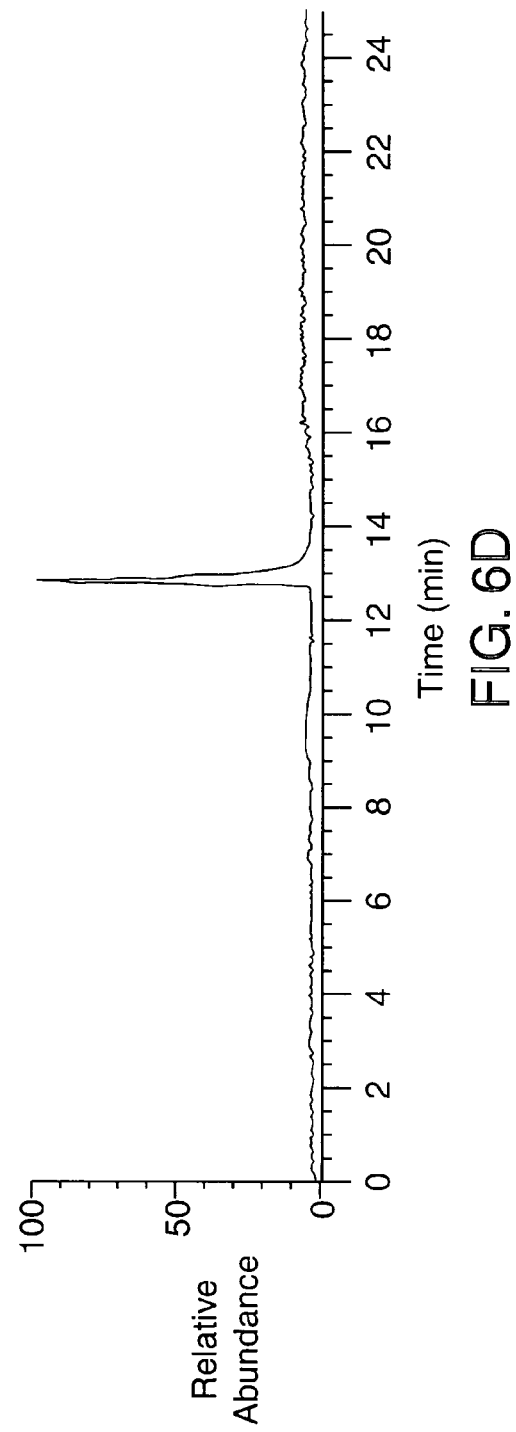
FIG. 6D shows a LC/MS/MS chromatogram of 250 μL Wm. Leman spearmint/peppermint residue (0.2 gram/mL) spiked with 10 μL MMS (62 μg/mL).
Figure 8A:
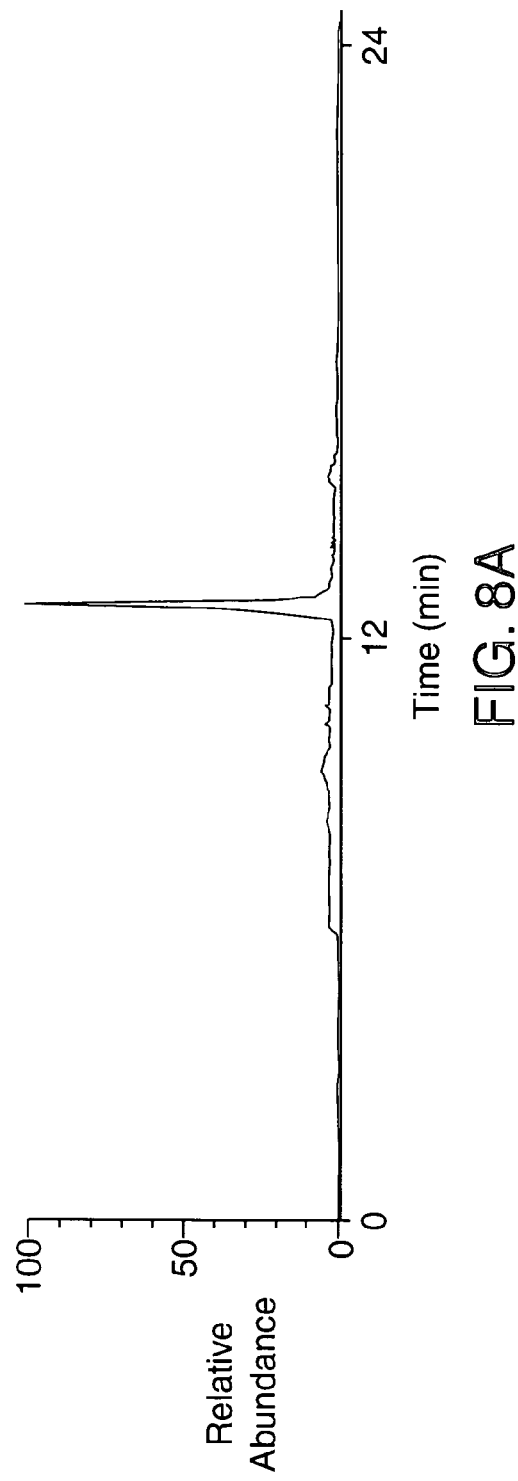
FIG. 8A shows a LC/MS/MS chromatogram of 0.68 μg/mL MMS.
Figure 8B:
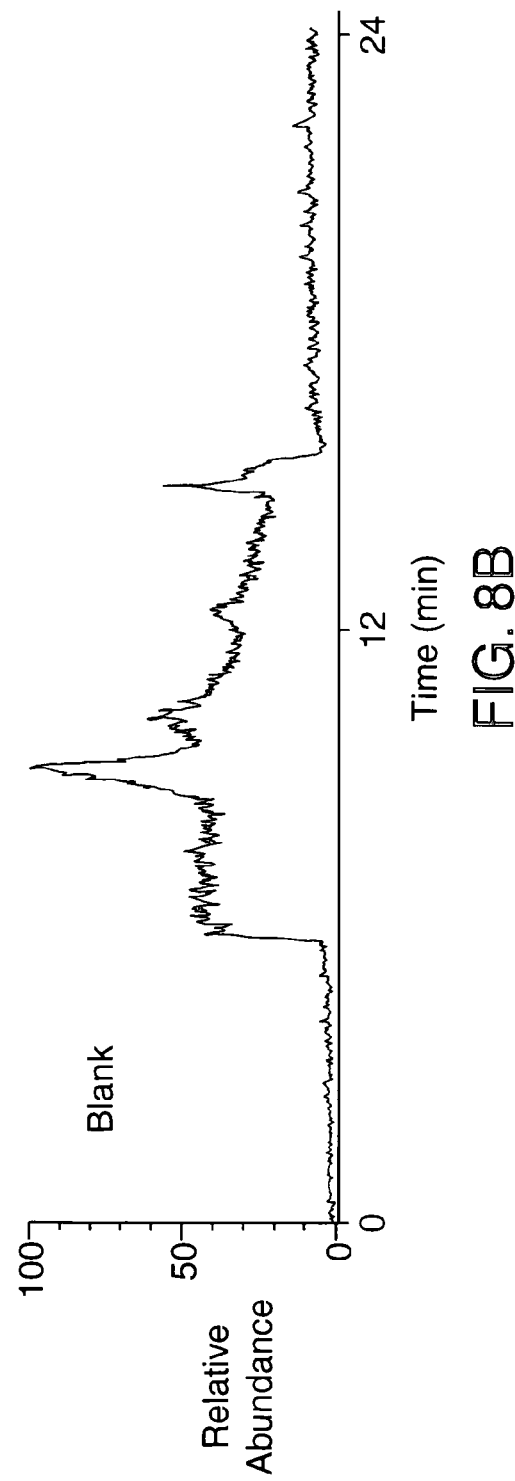
FIG. 8B shows a LC/MS/MS chromatogram of a blank (sample solvent).
Figure 8C:
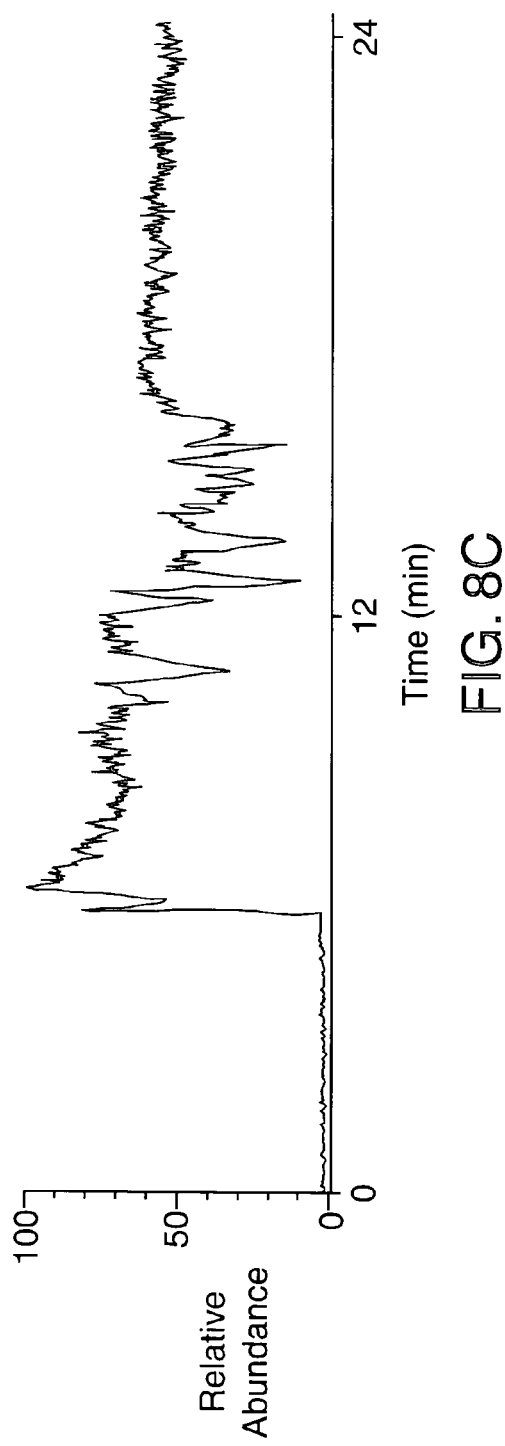
FIG. 8C shows a LC/MS/MS chromatogram of flour extract injected as is.
Figure 8D:
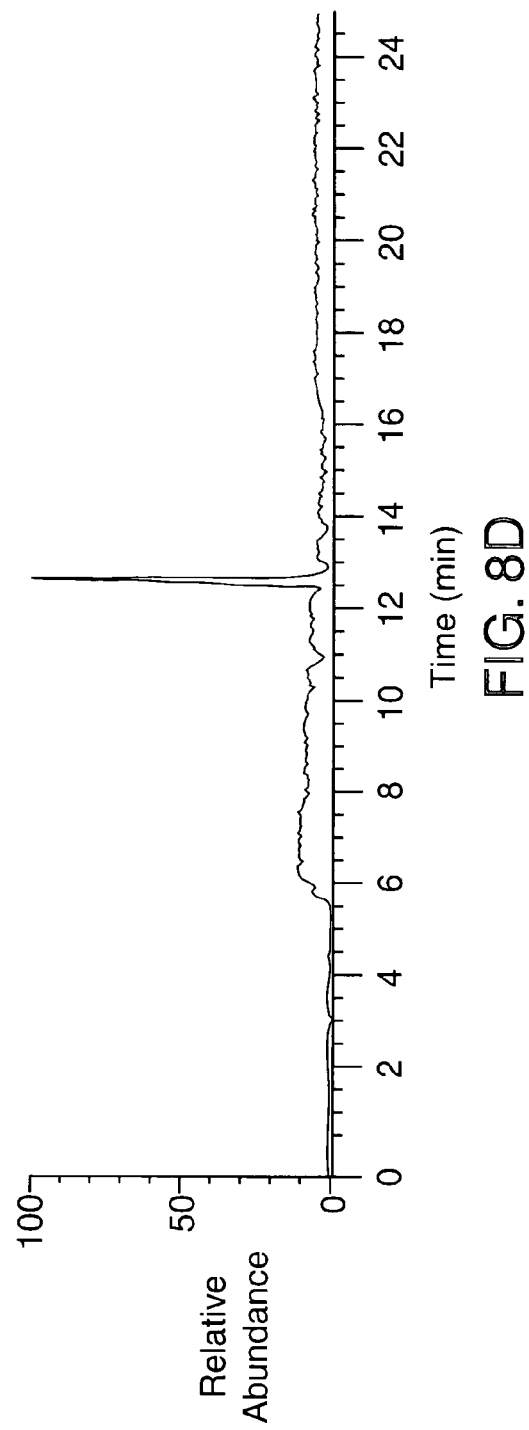
FIG. 8D shows a LC/MS/MS chromatogram of 250 μL flour extract spiked with 1 μL MMS (68 μg/mL).

A 0.86 gram sample of Wm. Leman spearmint/peppermint residue was diluted with 5.0 mL methanol for analysis (sample concentration=0.2 gram/mL assuming $d_{extract}$=1 gram/mL). FIG. 6 shows the results of this analysis.

A 200 gram sample of unbleached all-purpose flour was spiked with 3.9 milligram menthol and 5.7 milligram succinic acid, thoroughly blended, and extracted following the same procedure as described for *L. barbarum* and *M. piperita*. The extract was directly analyzed, without dilution, for the presence of MMS. FIG. 7 shows the results of this analysis.

A second 200 gram sample of flour was spiked with 2.0 milligram menthol plus 3.0 milligram succinic acid, thoroughly blended, and extracted as above. The extract was directly analyzed, without dilution, for the presence of MMS. FIG. 8 shows the results of this analysis.

EXAMPLE 2

| LC/MS/MS (SRM) INSTRUMENT CONDITIONS | |
|---|---|
| Instrument | Finnigan TSQ 7000 (API 2) interfaced to a SpectraSystem P4000 HPLC Pump |
| Column: | Zorbax 5 µm SB-C18 2.1 mm (ID) × 150 mm, Ser. No: CN 2051 |
| Mobile Phase A: | $H_2O$ (10 mM $NH_4OAc$) |
| Mobile Phase B: | $CH_3OH$ (10 mM $NH_4OAc$) |
| Gradient: | 10% B to 100% B in 10 minutes (hold 15 minutes) |
| Flow Rate: | 0.2 mL/minute |
| Injection Volume: | 20 µL |
| Ionization Mode: | -APCI (SRM) |
| Vaporizer Temperature: | 300 or 350° C. |
| Heated Capillary Temperature: | 200 or 250° C. |
| Sheath Gas ($N_2$): | 70 or 80 psi |
| Auxiliary Gas ($N_2$): | 0 or 20 (arbitrary units) |
| Coll. Cell (Ar): | 2 mT |
| Collision Energy: | +20 V |
| Precursor to Product Ion: | m/z 255/99 |

EXAMPLE 3

Preparation of Samples For Standard Addition Determination of MMS in *M. piperita* Extract A 2.37 gram sample of *M. piperita* extract was diluted with 2.0 mL methanol (sample concentration=0.54 gram/mL assuming $d_{extract}$=1 gram/mL). A 400 microliter of this solution was added to four vials. Vials 2–4 were spiked with MMS (84 µg/mL) according to Table 1. The data from this analysis are plotted in FIG. 9.

TABLE 1

| Vial | *M. piperita* (0.54 g/mL) µL added | MMS (84 µg/mL) µL added | CH₃OH µL added | MMS equivalent ppm |
|---|---|---|---|---|
| 1 | 400 | 0 | 30 | 0 |
| 2 | 400 | 10 | 20 | 3.9 |
| 3 | 400 | 20 | 10 | 7.8 |
| 4 | 400 | 30 | 0 | 11.7 |

EXAMPLE 4

Preparation of Samples For Standard Addition Determination of MMS in Flour Extract A 200 µL sample of flour extract was spiked with MMS according to Table 2. The data from this analysis are plotted in FIG. 10.

TABLE 2

| Vial | Flour extract µL added | MMS (84 µg/mL) µL added | MMS equivalent* ppm |
|---|---|---|---|
| 1 | 200 | 0 | 0 |
| 2 | 200 | 1 | 0.42 |
| 3 | 200 | 2 | 0.84 |
| 4 | 200 | 3 | 1.3 |

*assuming $d_{extract}$ = 1 gram/mL.

What is claimed is:

1. A composition comprising a plant extract containing between 0.5 and 1000 parts per million of monomenthyl succinate as a coolant, and wherein said plant extract is isolated from a plant of the genus *Lycium* or *Mentha*.

2. The composition of claim 1, wherein the plant extract is isolated from *Lycium barbarum* or *Mentha piperita*.

3. A method for isolating a plant extract containing monomenthyl succinate comprising:
   mixing plant biomass with 95% ethanol, wherein the plant biomass is from a selected plant of the genus *Lycium* or *Mentha*;
   extracting the mixture for 10 to 24 hours; and
   filtering the mixture to remove the plant biomass so that a plant extract containing monomenthyl succinate is isolated.

4. The composition of claim 3, wherein the selected plant is *Lycium barbarum* or *Mentha piperita*.

5. A plant extract containing monomenthyl succinate isolated by the method of claim 3.

6. The plant extract of claim 5, wherein said extract contains between 0.5 and 1000 parts per million of monomenthyl succinate.

* * * * *